United States Patent
Oko et al.

(10) Patent No.: US 10,391,190 B1
(45) Date of Patent: Aug. 27, 2019

(54) MODULAR TRAY AND BRACKET ASSEMBLY FOR EQUIPMENT STERILIZATION

(71) Applicant: K1 Medical Technologies, LLC, Woodbridge, CT (US)

(72) Inventors: Walter J. Oko, Woodbridge, CT (US); Scott E. Cohen, Siesta Key, FL (US)

(73) Assignee: K1 Medical Technologies, LLC, Woodbridge, CT (US)

( * ) Notice: Subject to any disclaimer, the term of this patent is extended or adjusted under 35 U.S.C. 154(b) by 0 days.

(21) Appl. No.: 16/116,302

(22) Filed: Aug. 29, 2018

Related U.S. Application Data

(60) Provisional application No. 62/633,429, filed on Feb. 21, 2018.

(51) Int. Cl.
| | |
|---|---|
| A47B 96/06 | (2006.01) |
| A61L 2/26 | (2006.01) |
| F16B 2/22 | (2006.01) |
| A61L 2/07 | (2006.01) |
| A61B 50/33 | (2016.01) |

(52) U.S. Cl.
CPC .......... *A61L 2/26* (2013.01); *A61L 2/07* (2013.01); *F16B 2/22* (2013.01); *A61B 50/33* (2016.02); *A61L 2202/24* (2013.01)

(58) Field of Classification Search
CPC .......... A61L 2/26; A61L 2/07; A61L 2202/24; F16B 2/22; A61B 50/33
USPC .......... 248/220.41, 220.43, 222.11; 206/477; 211/85.13; 422/297
See application file for complete search history.

(56) References Cited

U.S. PATENT DOCUMENTS

| | | | | |
|---|---|---|---|---|
| 5,294,413 A * | 3/1994 | Riihimaki | ............... | A61L 2/26 206/263 |
| 6,244,447 B1 * | 6/2001 | Frieze | ............... | A61L 2/07 206/370 |
| 6,382,575 B1 * | 5/2002 | Frush | ............... | A61L 2/26 211/85.13 |
| 6,481,583 B1 * | 11/2002 | Black | ............... | A47F 5/0815 211/70.6 |
| 2005/0249651 A1 * | 11/2005 | Riley | ............... | A61L 2/26 422/300 |
| 2008/0116095 A1 * | 5/2008 | Riley | ............... | A61L 2/26 206/363 |
| 2013/0319888 A1 | 12/2013 | Birkbeck et al. | | |

OTHER PUBLICATIONS

U.S. Appl. No. 62/633,429, filed Feb. 21, 2018.

* cited by examiner

*Primary Examiner* — Gwendolyn W Baxter
(74) *Attorney, Agent, or Firm* — McCarter & English, LLP

(57) ABSTRACT

A tray and bracket assembly are provided that are configured and adapted to promote modularity and withstand the harsh environment of central sterile processing processes. The modular bracket assembly may be removed and relocated on the tray without additional fasteners or components. The tray and bracket assembly may further provide identification features to correctly associate cataloged reusable medical devices to identified trays.

30 Claims, 22 Drawing Sheets

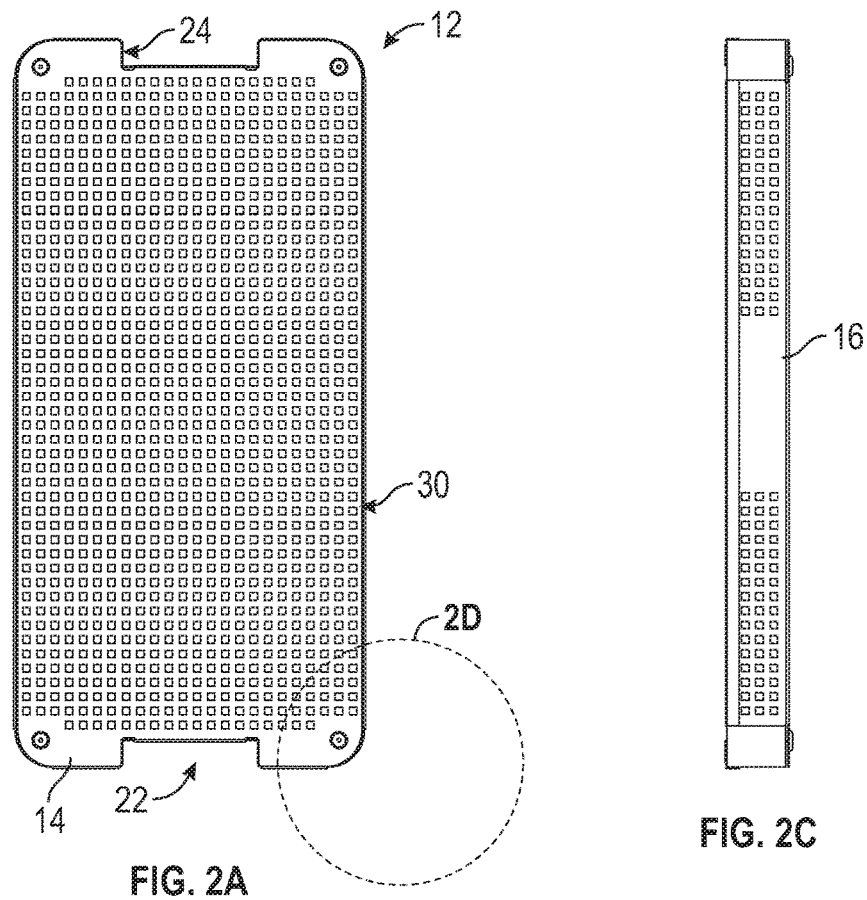
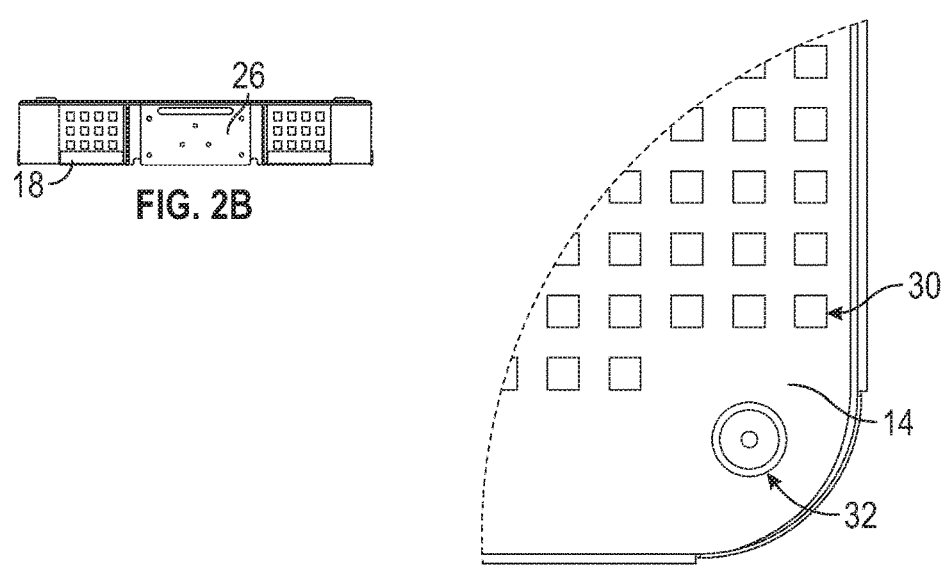

MODULAR TRAY AND BRACKET ASSEMBLY FOR EQUIPMENT STERILIZATION

CROSS-REFERENCE TO RELATED APPLICATIONS

This application claims priority benefit to a provisional patent application entitled "Modular Tray and Bracket Assembly for Equipment Sterilization, which was filed on Feb. 21, 2018, and assigned Ser. No. 62/633,429. The foregoing provisional patent application is incorporated herein by reference in its entirety.

FIELD OF THE DISCLOSURE

The present disclosure generally relates to tray mountable bracket(s) and, more generally, a modular sterilization tray and bracket system for detachably retaining reusable medical devices.

BACKGROUND OF THE DISCLOSURE

Sterilization trays provide a container for retaining reusable medical devices during a patient's surgical procedure (e.g., during the perioperative process, which may include preoperative care, intraoperative care, and postoperative care) and/or during the central sterile processing process (e.g., autoclave-based steam sterilization). Included within the central sterile processing process are the steps of decontamination, cleaning, assemble and pack, sterilization, storage, distribution/transportation, and aseptic presentation. In hospitals and other health care facilities, a sterile processing department (e.g., Central Sterile Services Department) performs sterilization and other actions on medical devices, equipment, and consumables for subsequent use by medical professionals in the operating room of the hospital (or other health care facility) and also for other aseptic procedures.

Sterilization trays may include a cover, a base, and one or more attachment mechanisms for retaining reusable medical devices. After central sterile processing, sterilization trays may be brought into the operating room, or other venue, to provide a "tool box" for medical professionals to work out of. Despite being used by medical professionals as a "tool box", sterilization trays provide no feedback, instruction, or ease of modularity to assist medical professionals.

Based on the foregoing, a need exists for an effective modular "tool box" that offers flexibility and reliability in the positioning of reusable medical devices in connection with the perioperative process, the central sterile processing process, and/or subsequent access to/use of the sterilized reusable medical devices. Thus, an interest exists for modular sterilization trays and brackets, and related methods of use. These and other inefficiencies and opportunities for improvement are addressed and/or overcome by the assemblies, systems and methods of the present disclosure.

SUMMARY OF THE DISCLOSURE

The present disclosure provides an advantageous assembly for detachably retaining devices relative to a container (e.g., a tray). In particular, the present disclosure is directed to systems/methods for detachably retaining reusable medical devices and other instruments during the perioperative process and/or during the central sterile processing process. Even more particularly, exemplary assemblies are disclosed that include a tray with at least one modular bracket assembly mounted directly or indirectly thereto, for detachable retention of reusable medical devices and/or instruments to facilitate use/exposure during the perioperative process and the central sterile processing process.

As used throughout, the term "reusable medical device," "medical device," or any combination thereof, includes an instrument, apparatus, implement, machine, contrivance, implant, in vitro reagent, or other similar or related article, including a component part, accessory, lab equipment, reagent, or test kit, as will be known to a person skilled in the art. The above definition of a reusable medical device is intended to be broader than the definition provided by the United States Food and Drug Administration (e.g., https://www.fda.gov/MedicalDevices/DeviceRegulationandGuidance/Overview/ClassifyYourDevice/ucm051512.htm).

Although the reusable medical device is referenced for use during surgery, additional instruments and/or devices that require central sterile processing, but are not used in connection with surgery, are expressly included in the present disclosure. Central sterile processing may include autoclave steam sterilization, which combines heat, humidity, and elevated pressure to sterilize a medical device. As used herein, a "user" generally refers to a human or a non-human and, in the case of a non-human, the term "user" generally refers to systems and devices that constitute and/or are controlled, in whole or in part, by software, artificial intelligence, robots and/or recognition software/machines.

In exemplary embodiments, the present disclosure provides an advantageous tray and bracket assembly that is configured and adapted to promote modularity and withstand the harsh environment of a central sterile processing process. Exemplary modular bracket assemblies according to the present disclosure may be removed and relocated relative to a tray without additional fasteners or components. The disclosed tray and bracket assembly may further provide identification features to associate cataloged reusable medical devices to identified trays.

Any combination or permutation of features, functions and/or embodiments as disclosed herein is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

BRIEF DESCRIPTION OF DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure.

Figure 1:
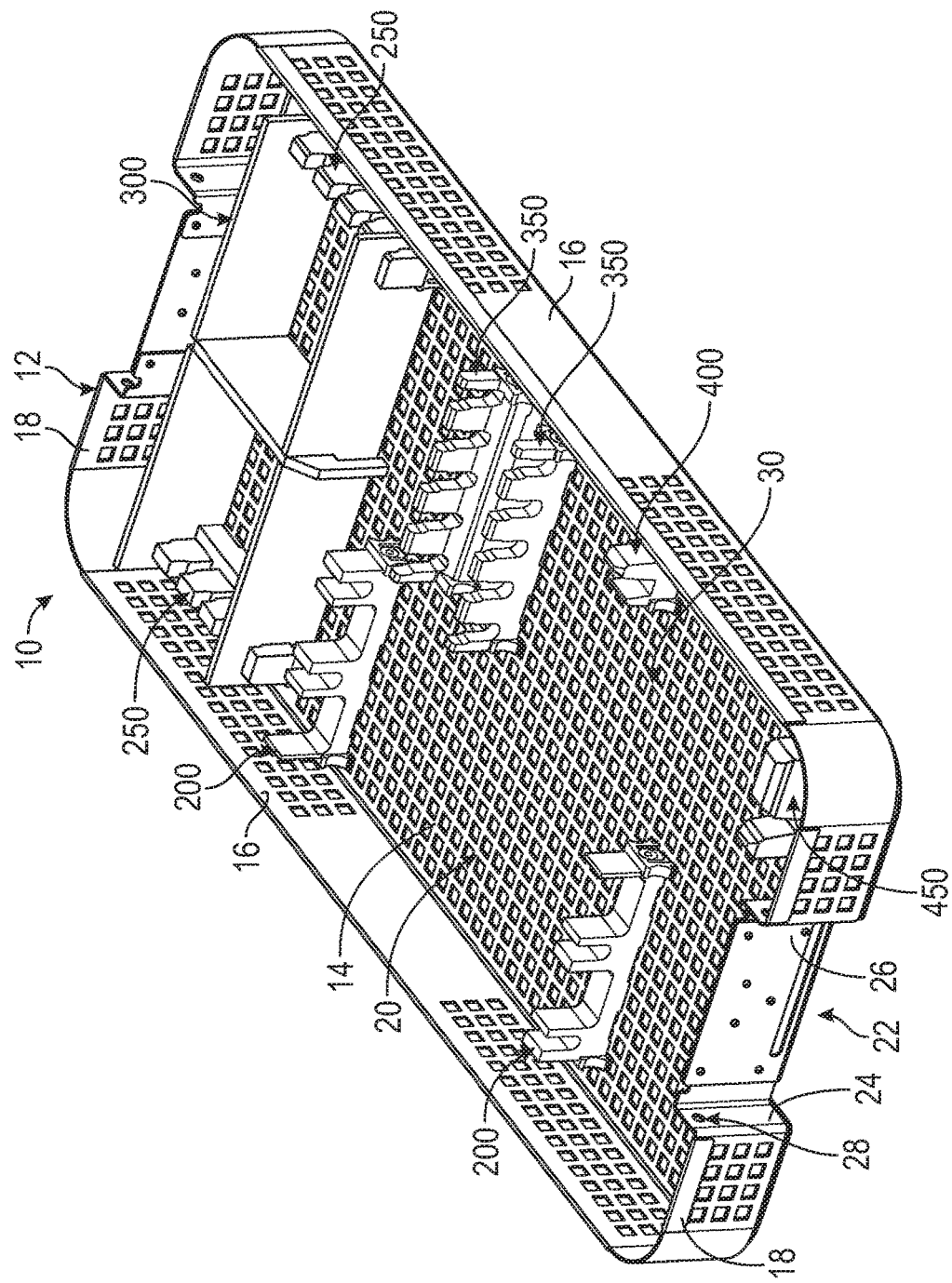
Figure 3B:
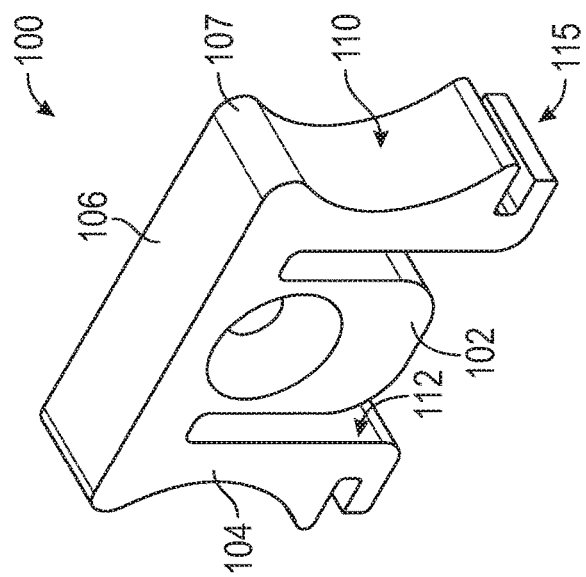
Figure 3A:
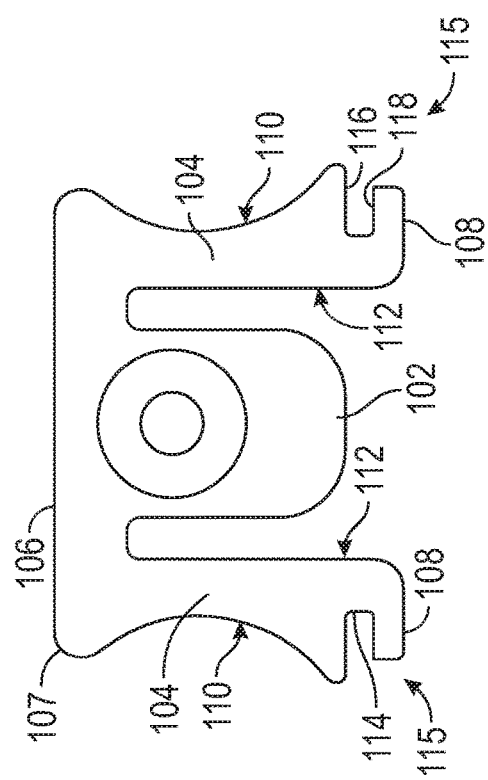
Figure 4:
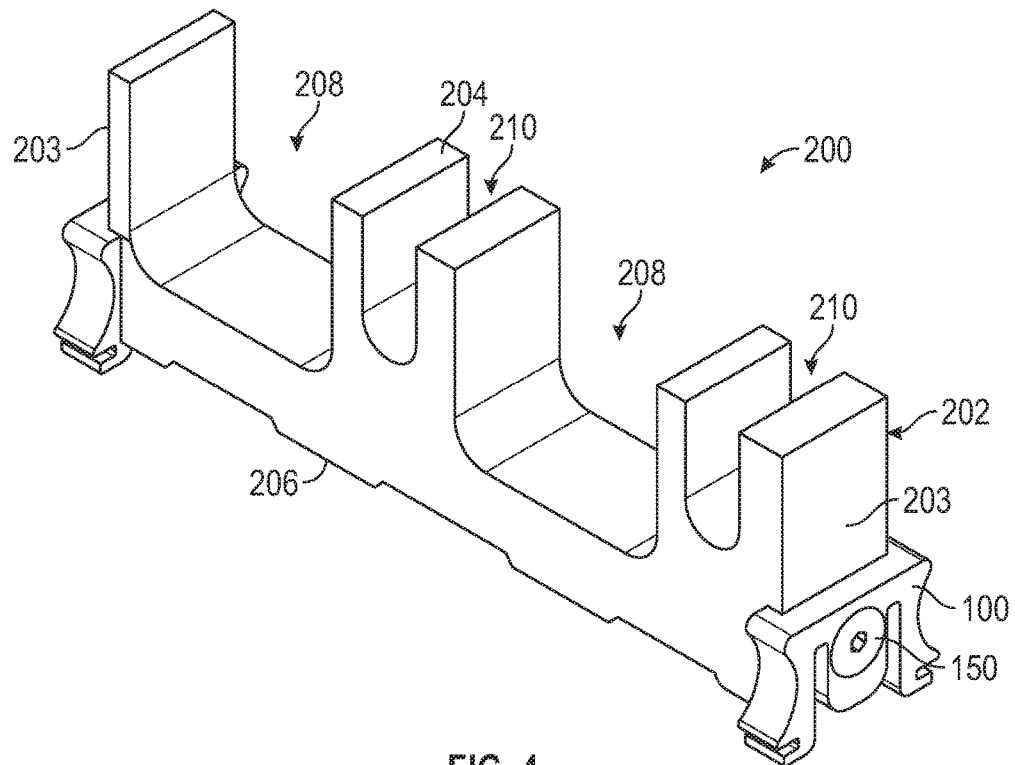
Figure 5:
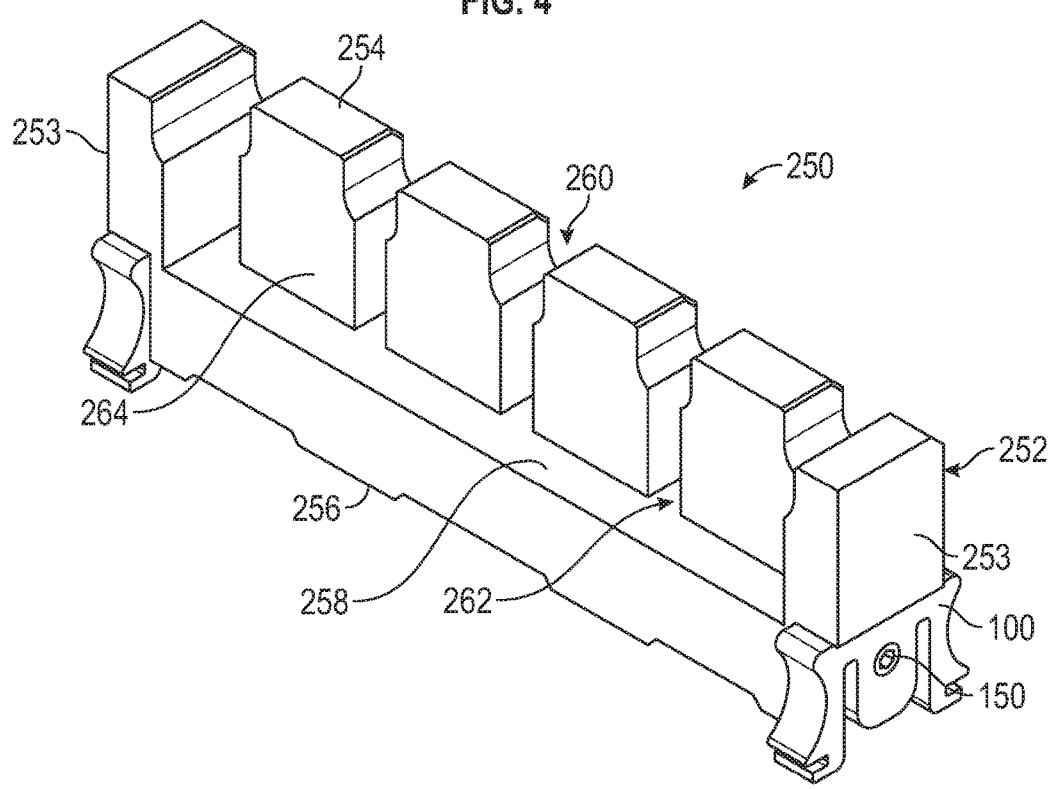
Figure 6A:
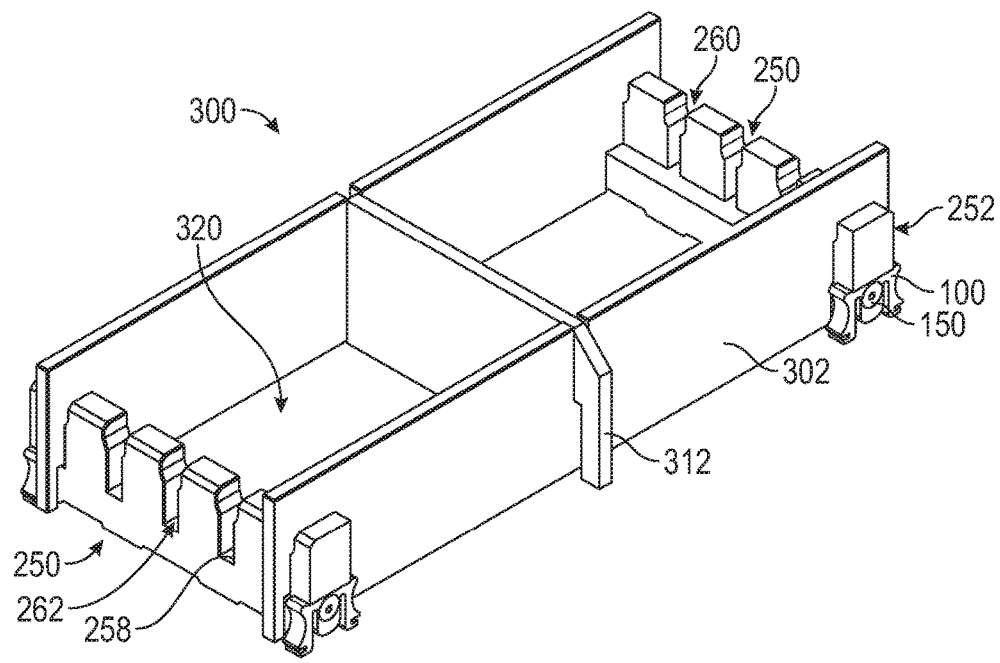
Figure 6B:
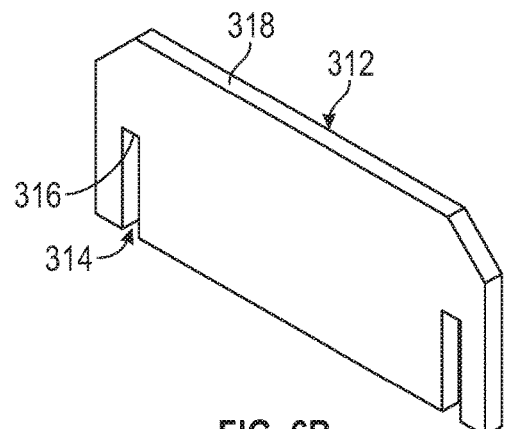
Figure 6C:
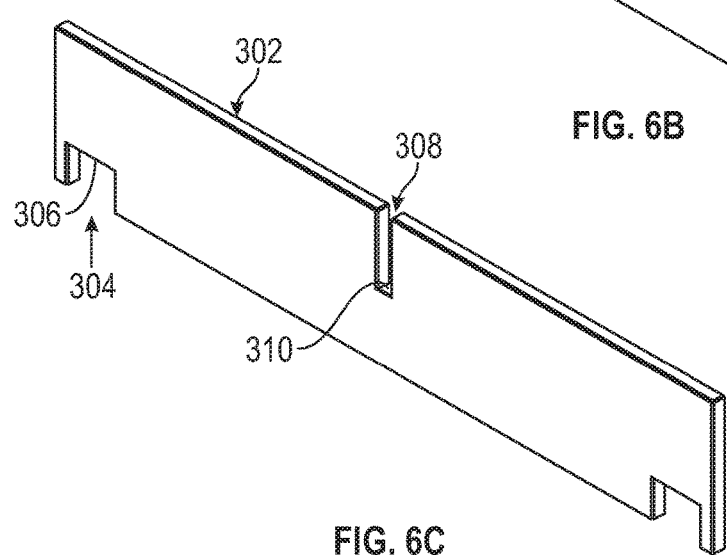
Figure 7:
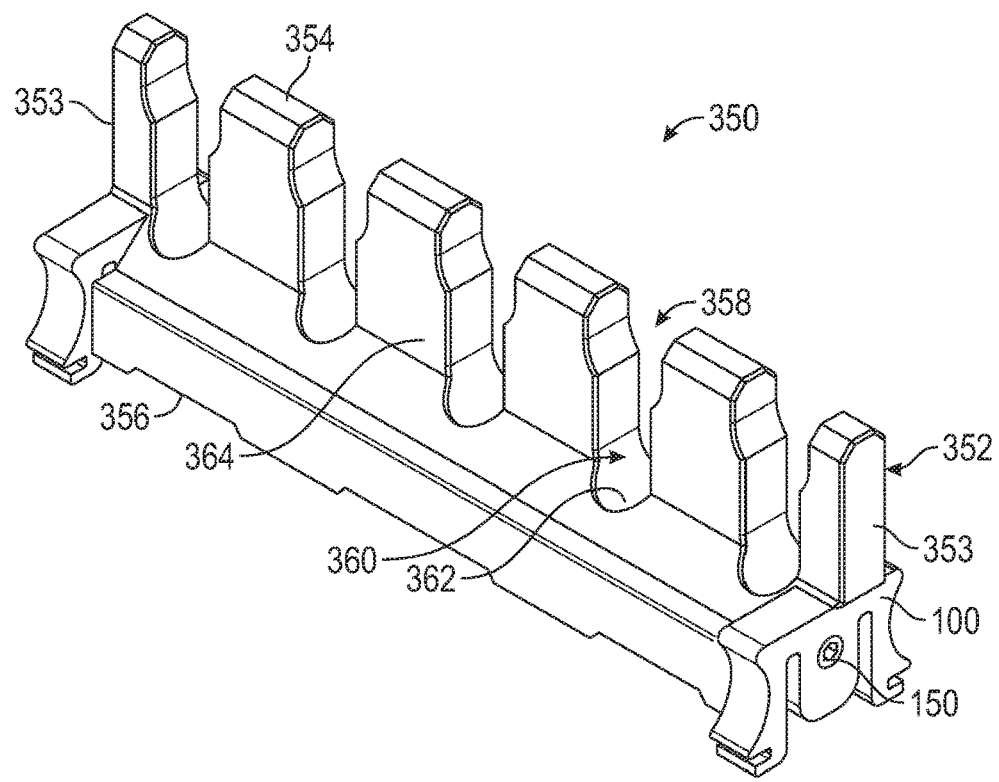
Figure 8:
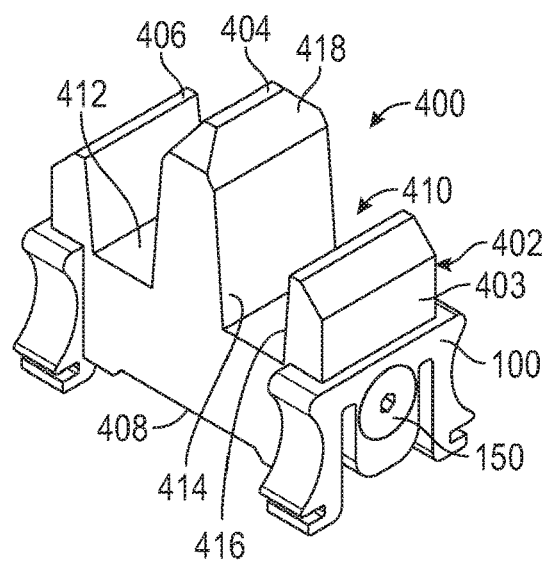
Figure 9:
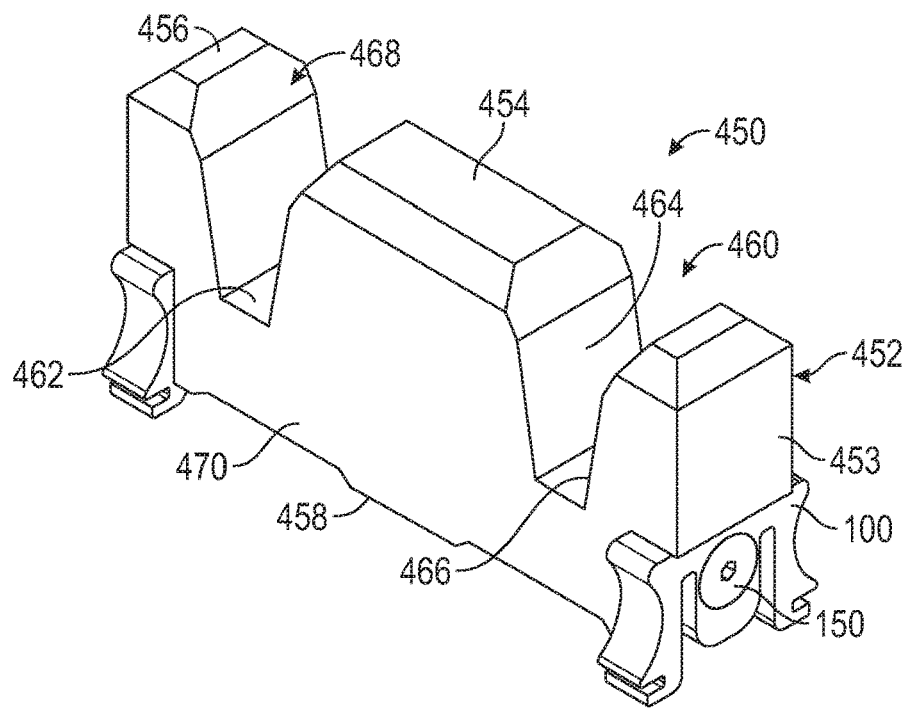
Figure 10:
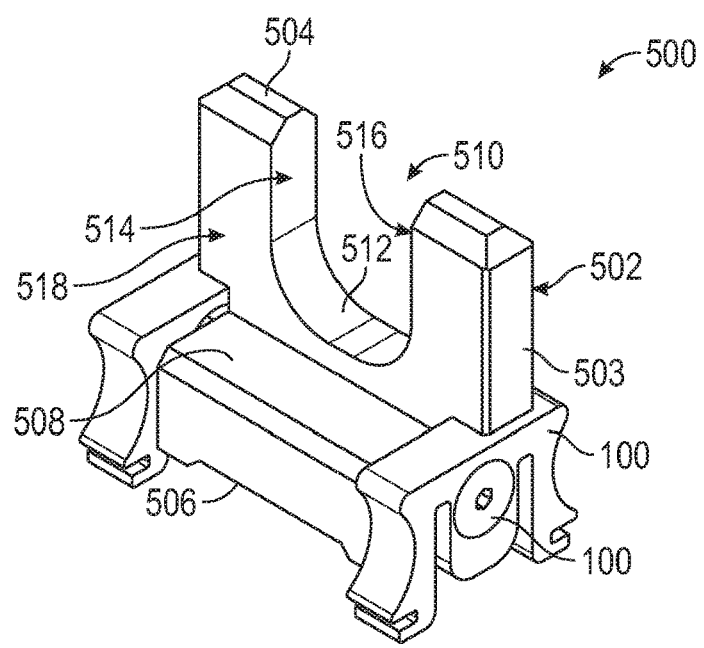
Figure 11:
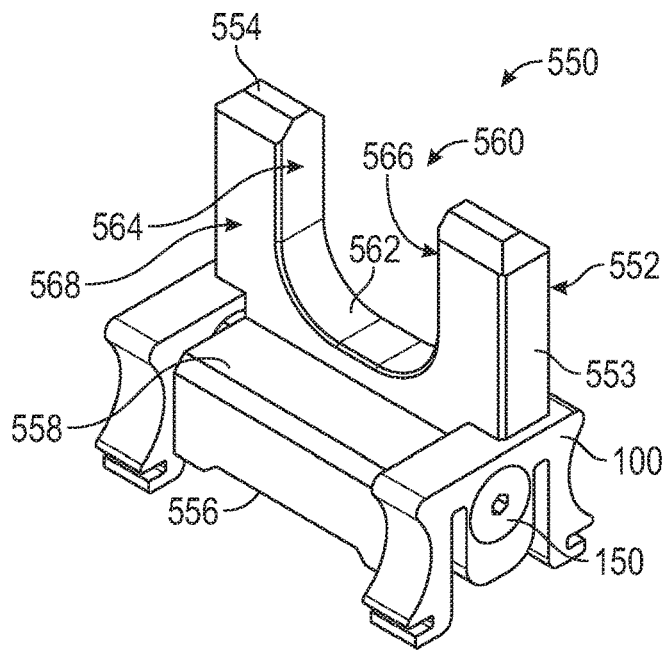
Figure 12:
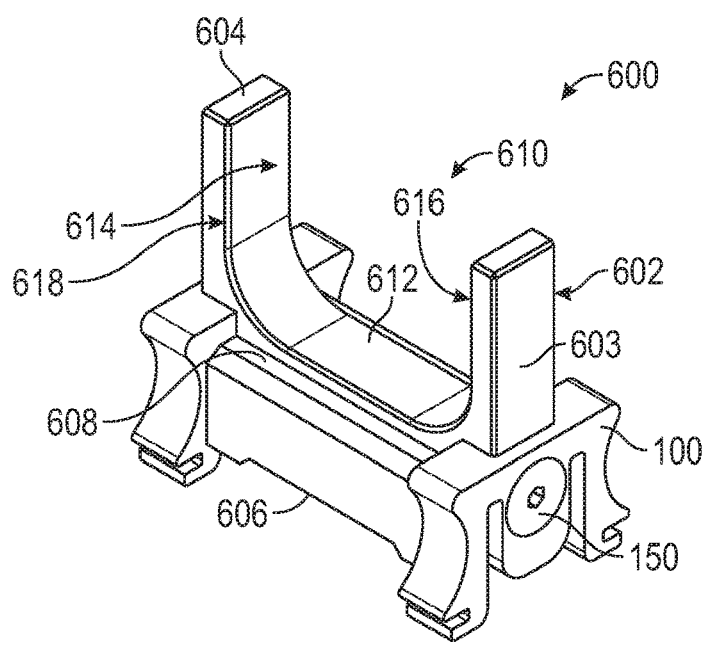
Figure 13:
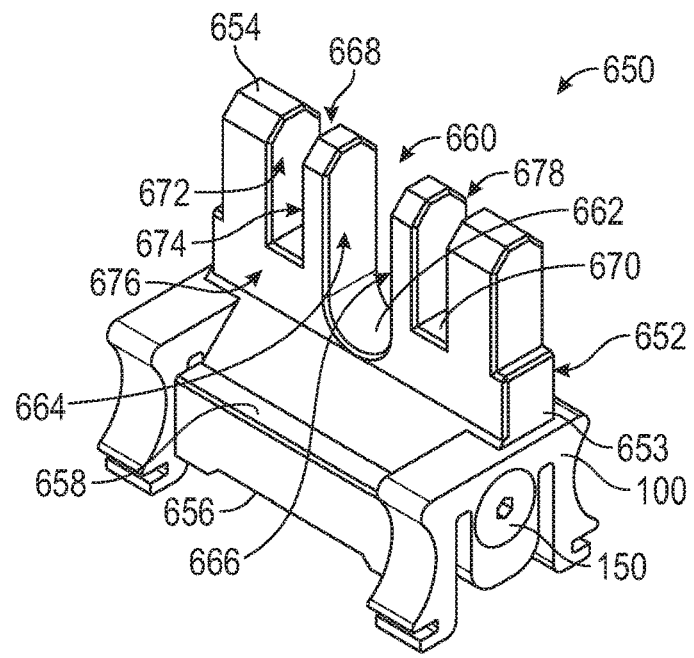
Figure 14:
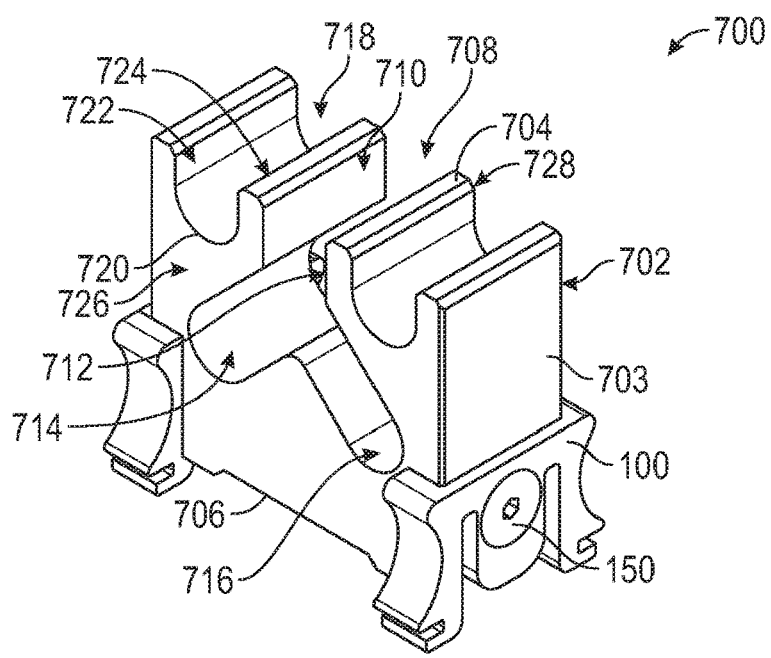
Figure 15:
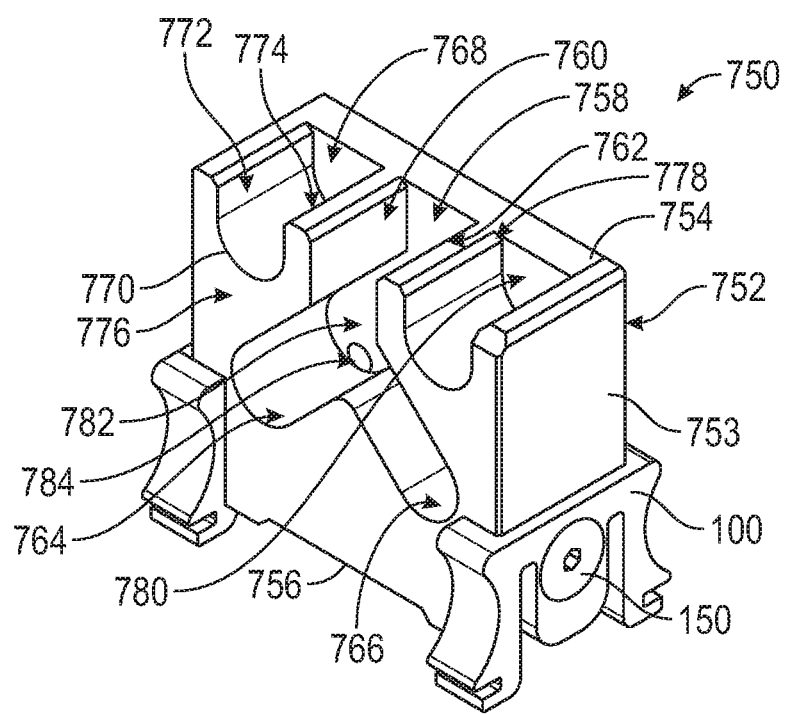
Figure 16A:
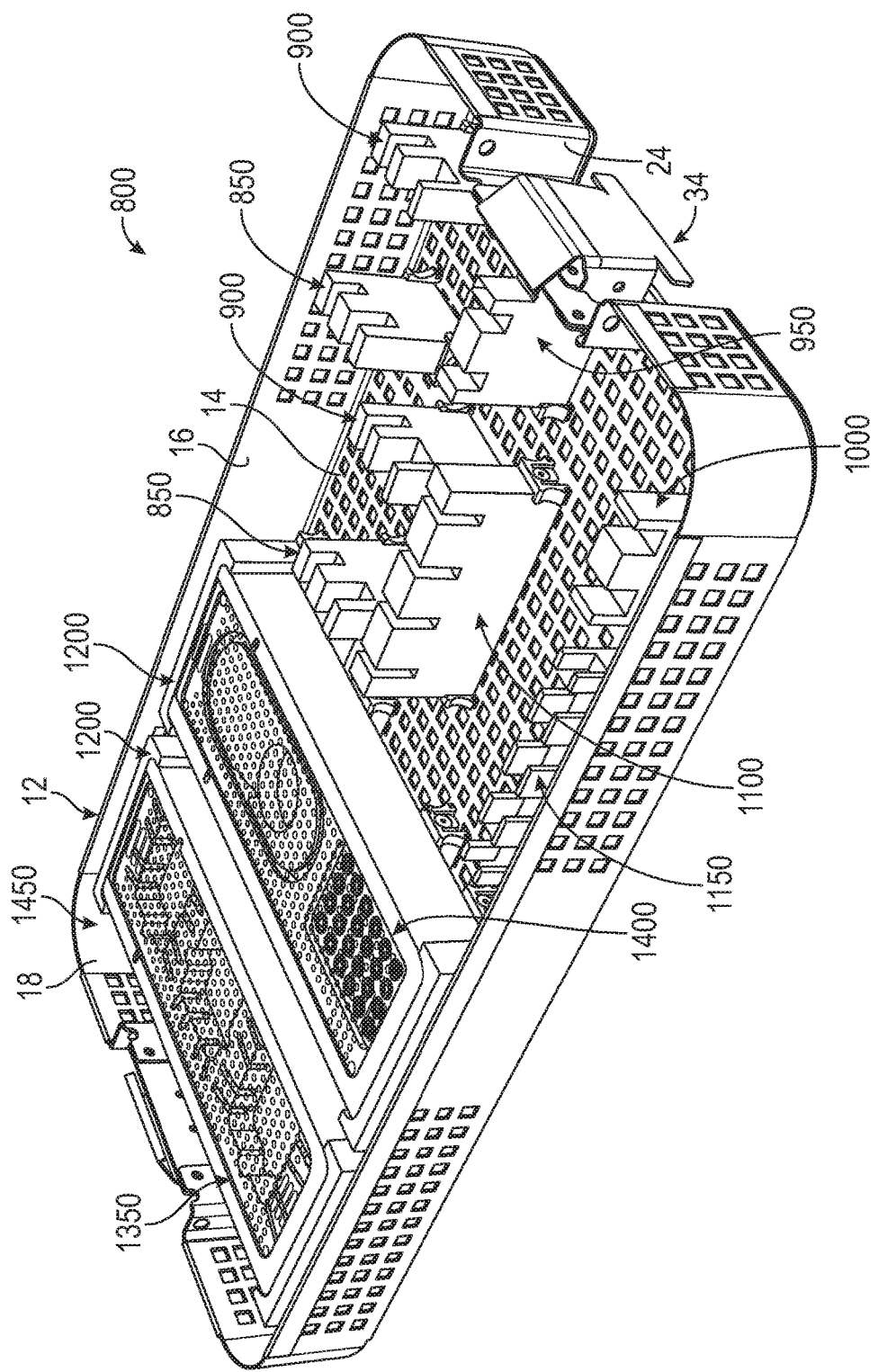
Figure 16B:
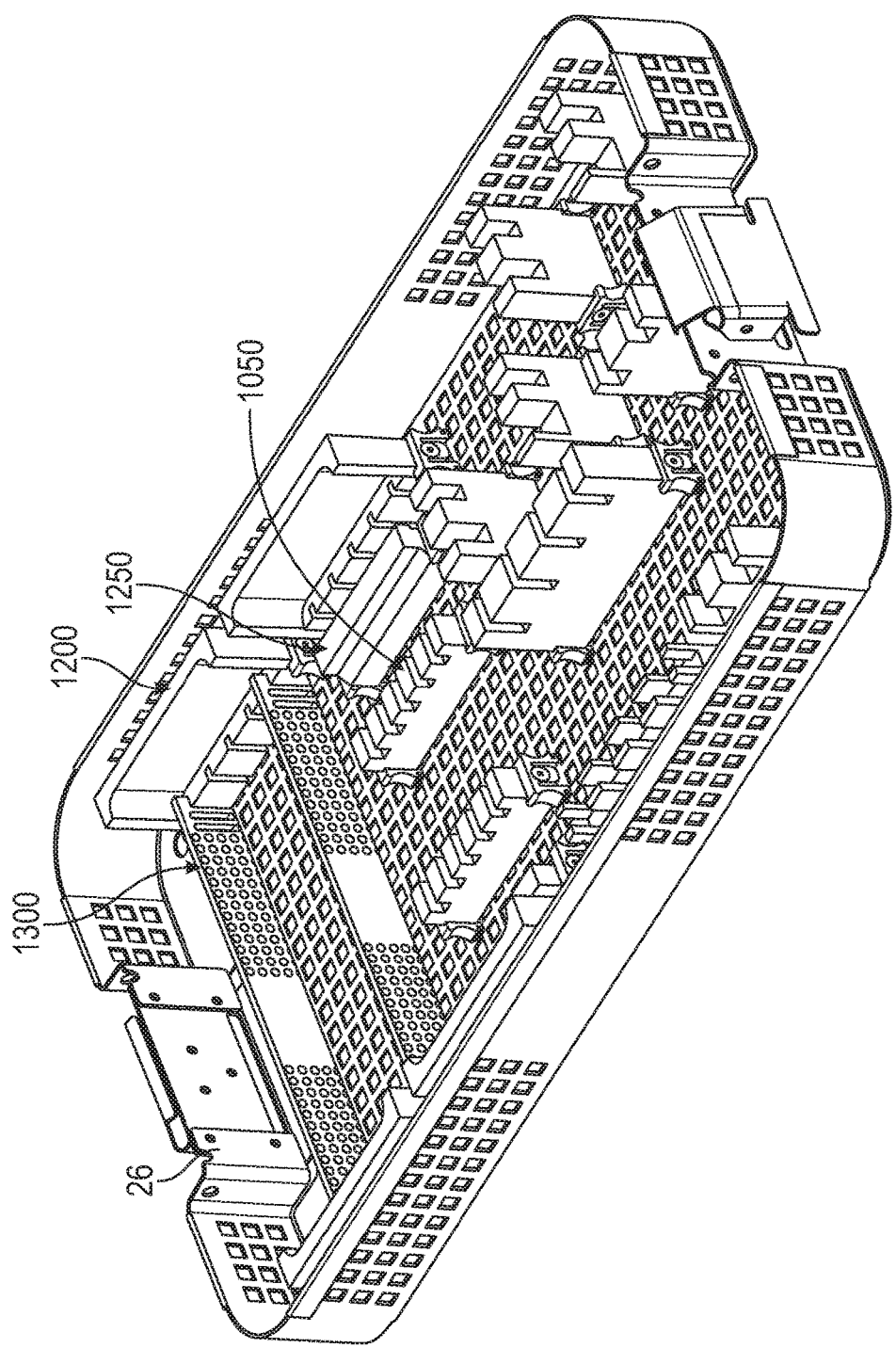
Figure 16C:
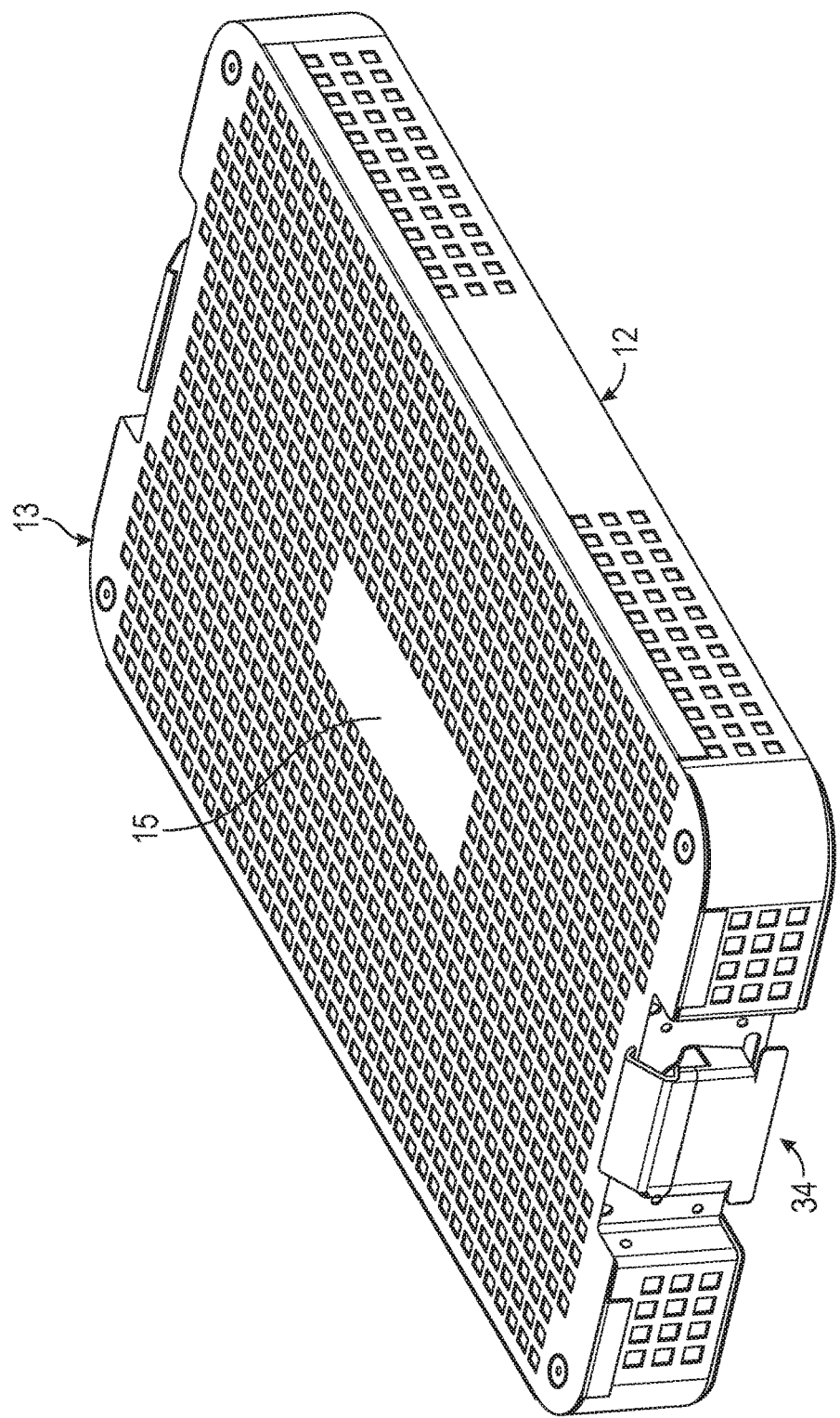
Figure 17:
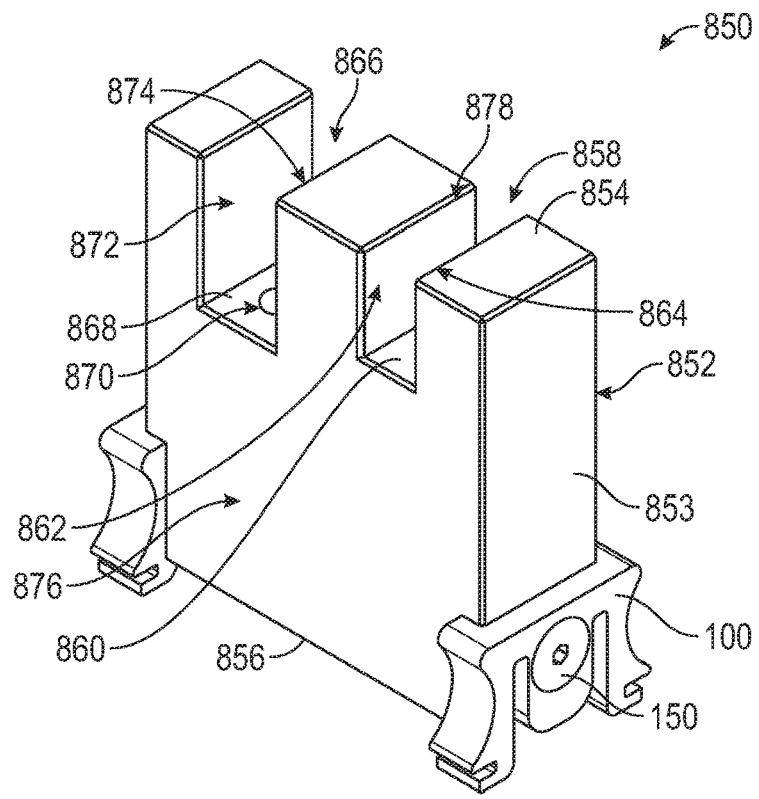
Figure 18:
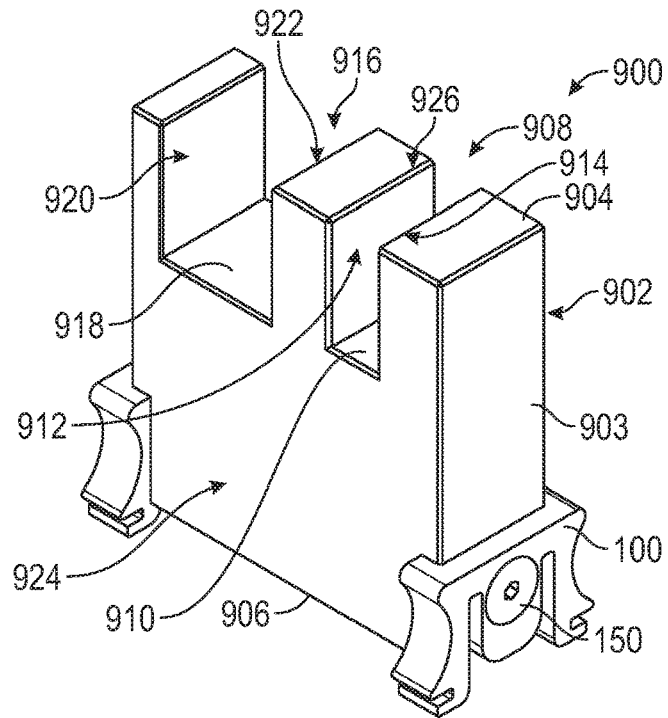
Figure 19:
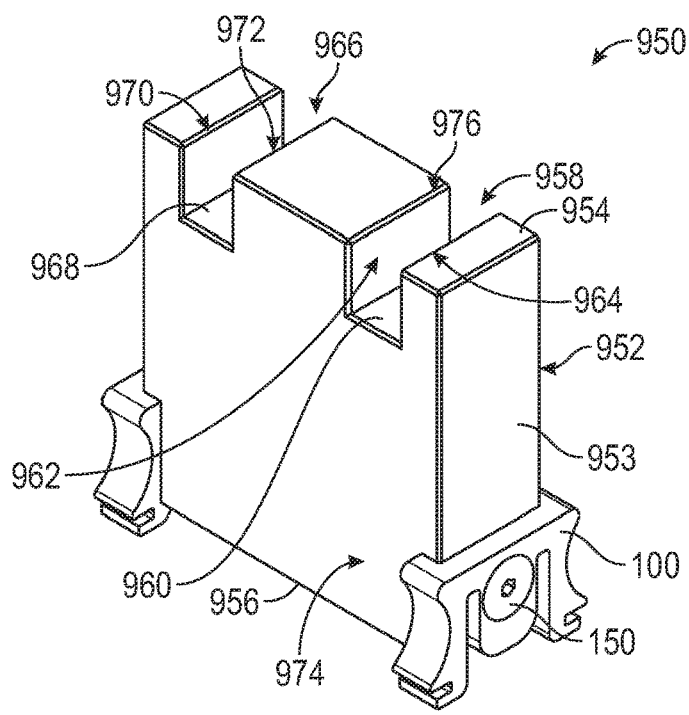
Figure 20:
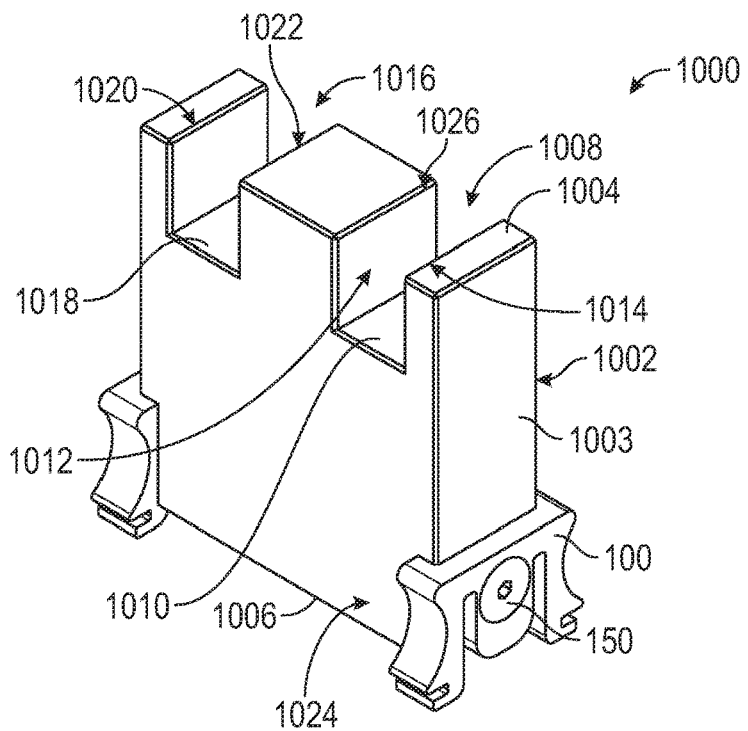
Figure 21:
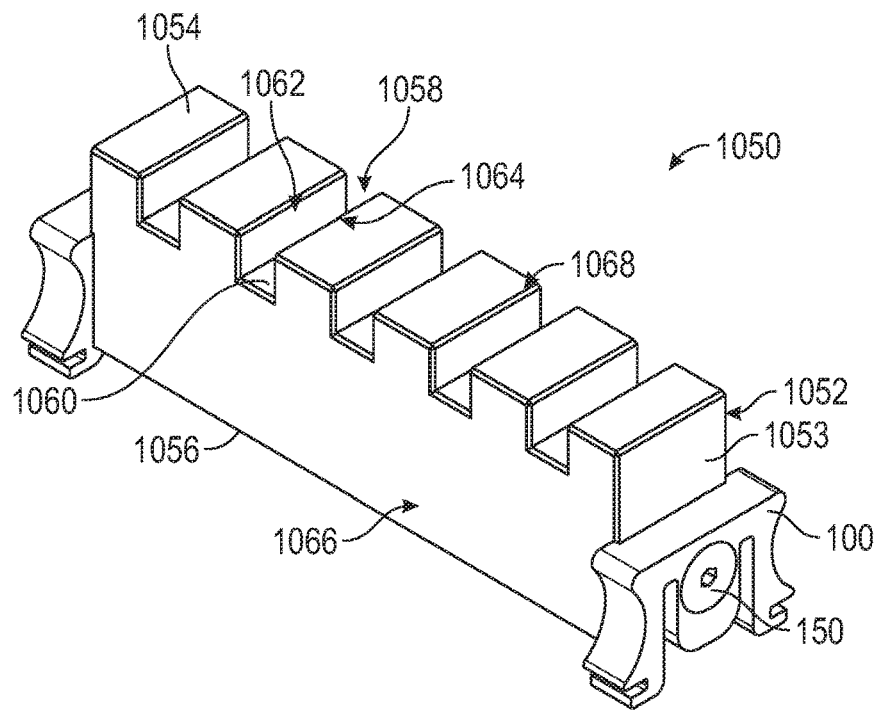
Figure 22:
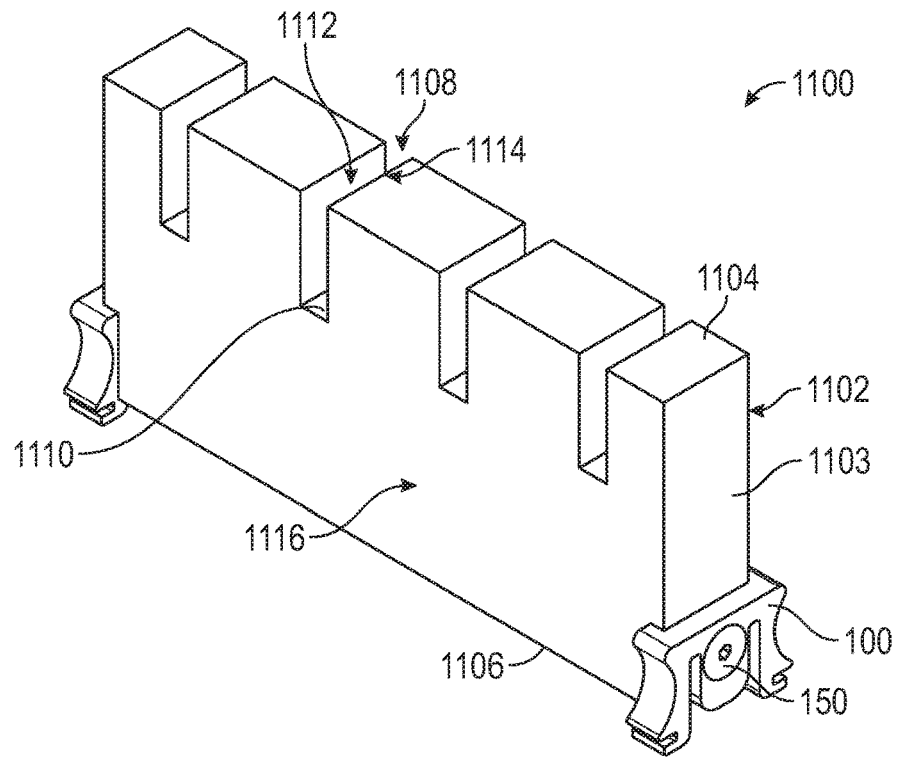
Figure 23:
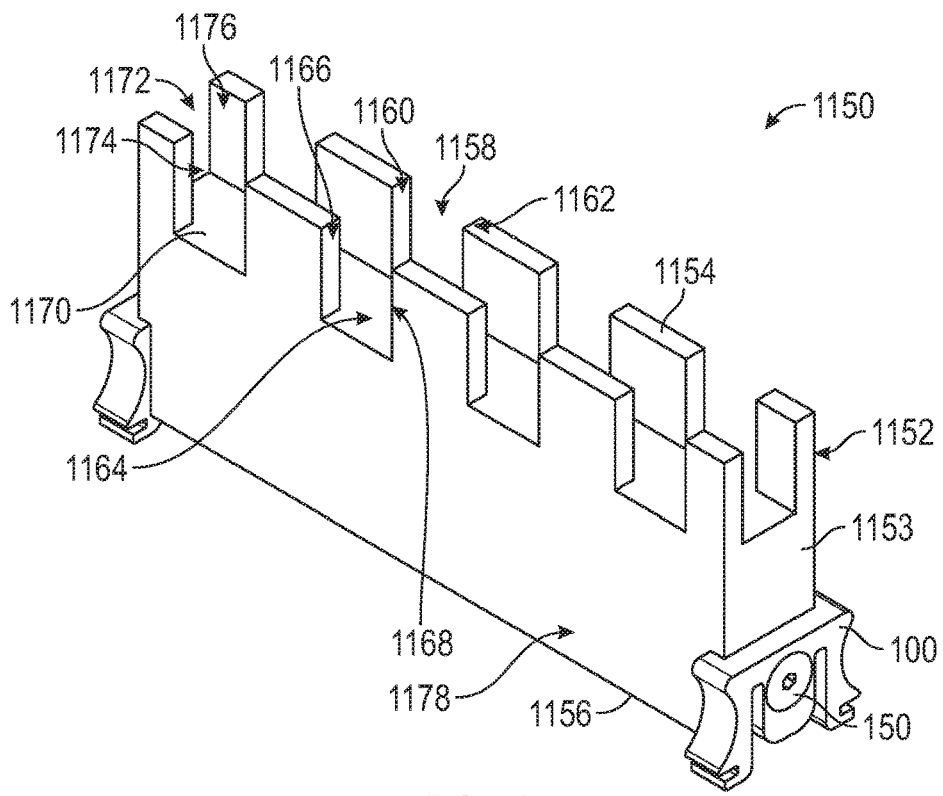
Figure 24:
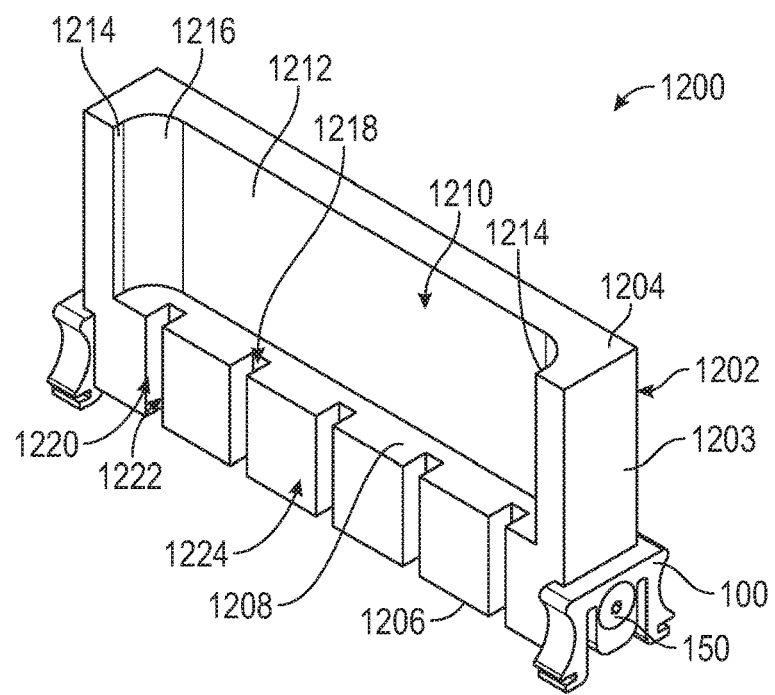
Figure 25:
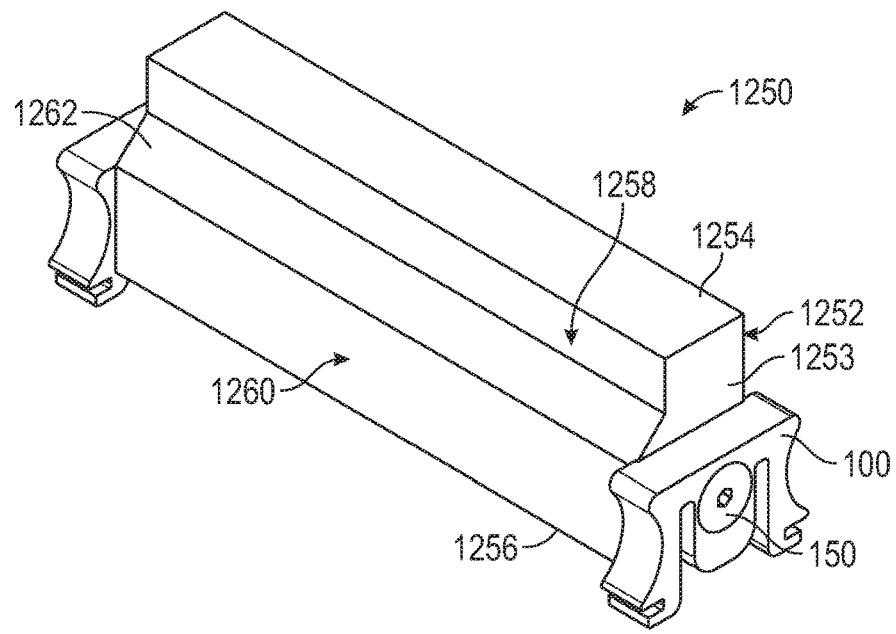
Figure 26:
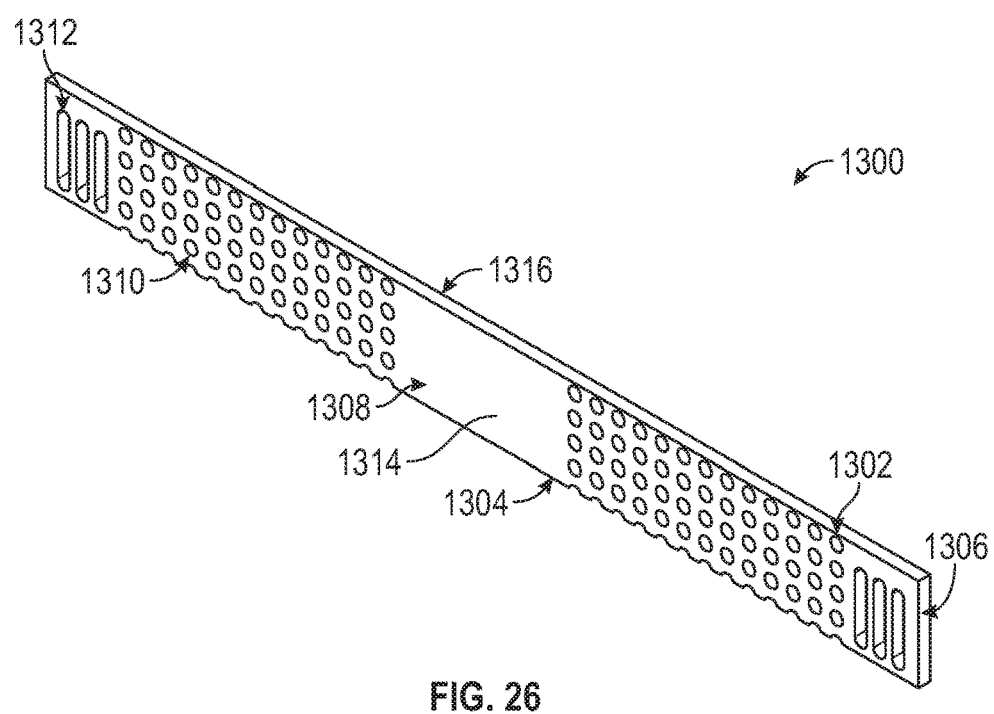
Figure 27A:
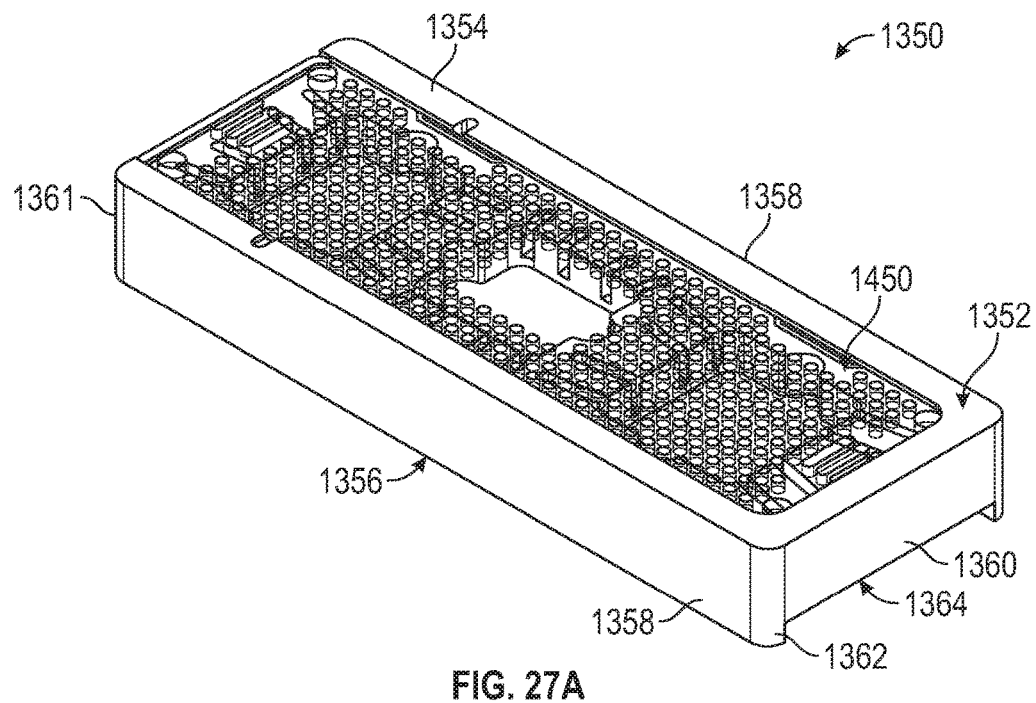
Figure 27B:
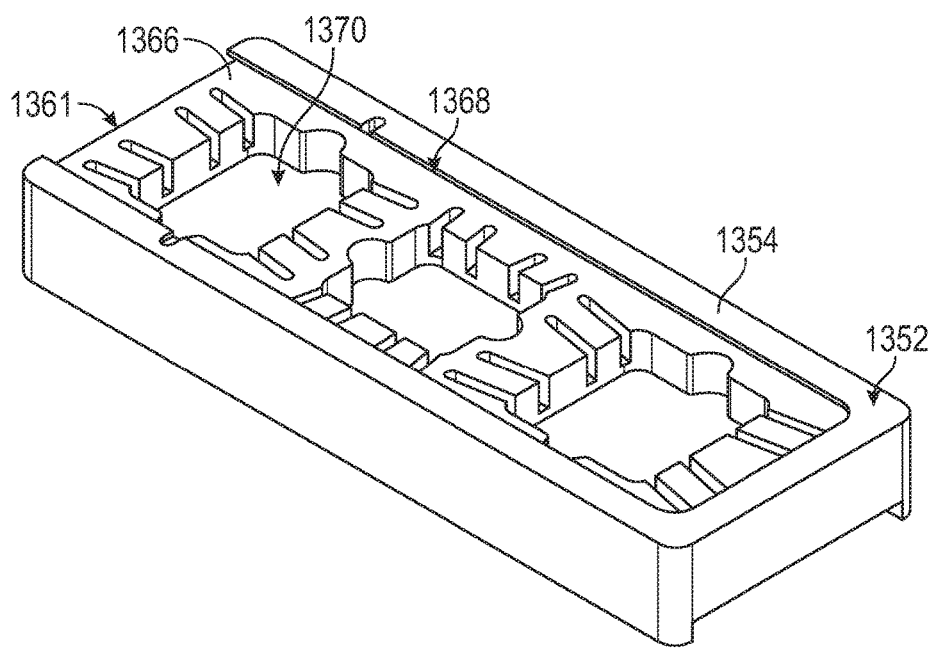
Figure 28A:
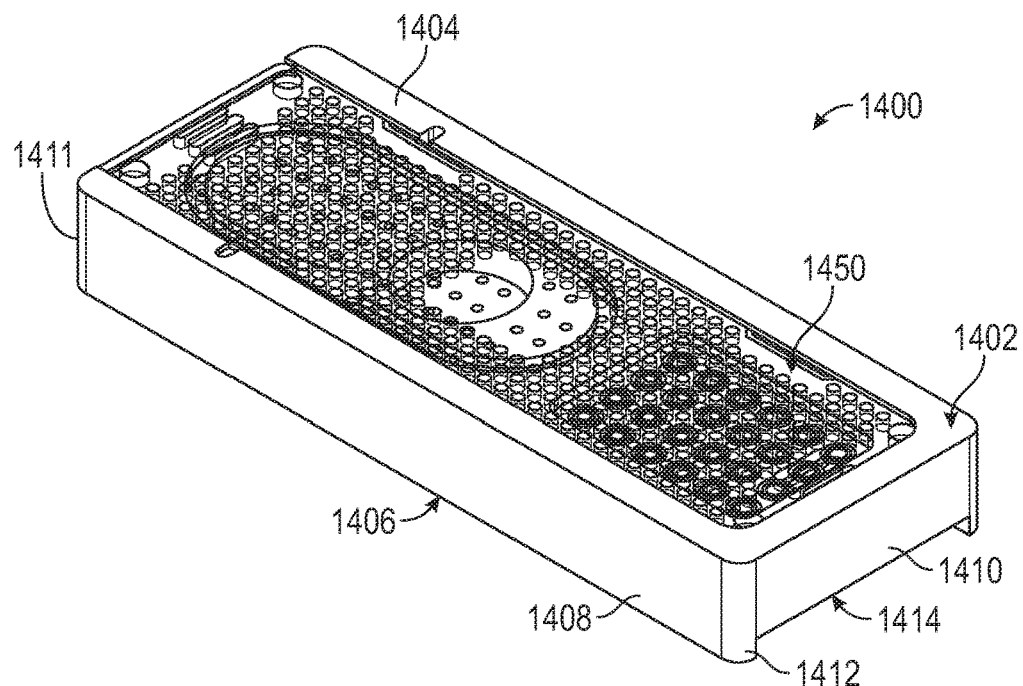
Figure 28B:
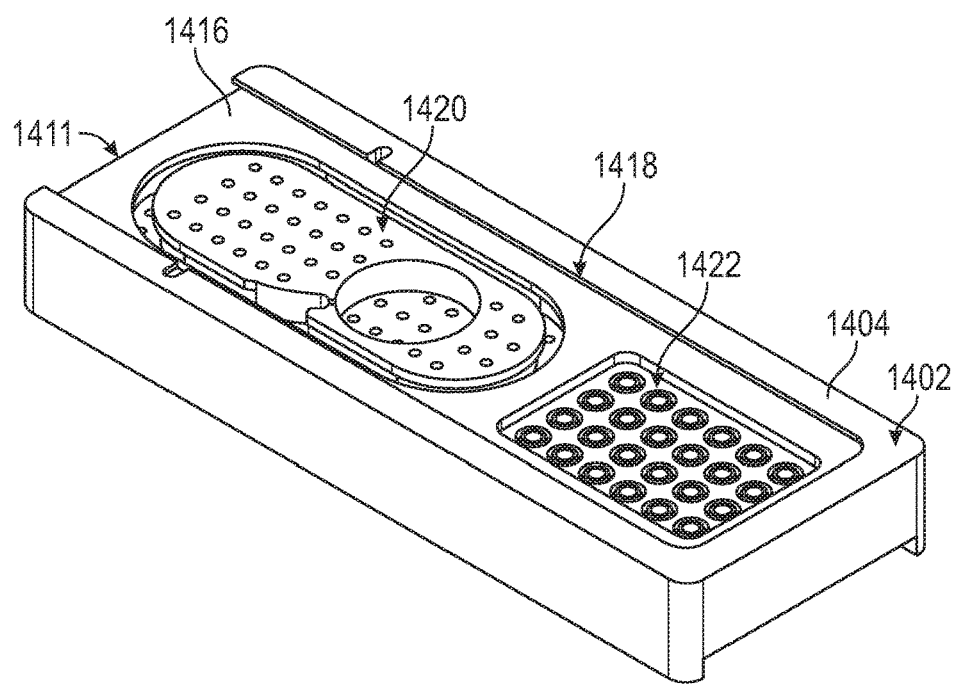
Figure 29:
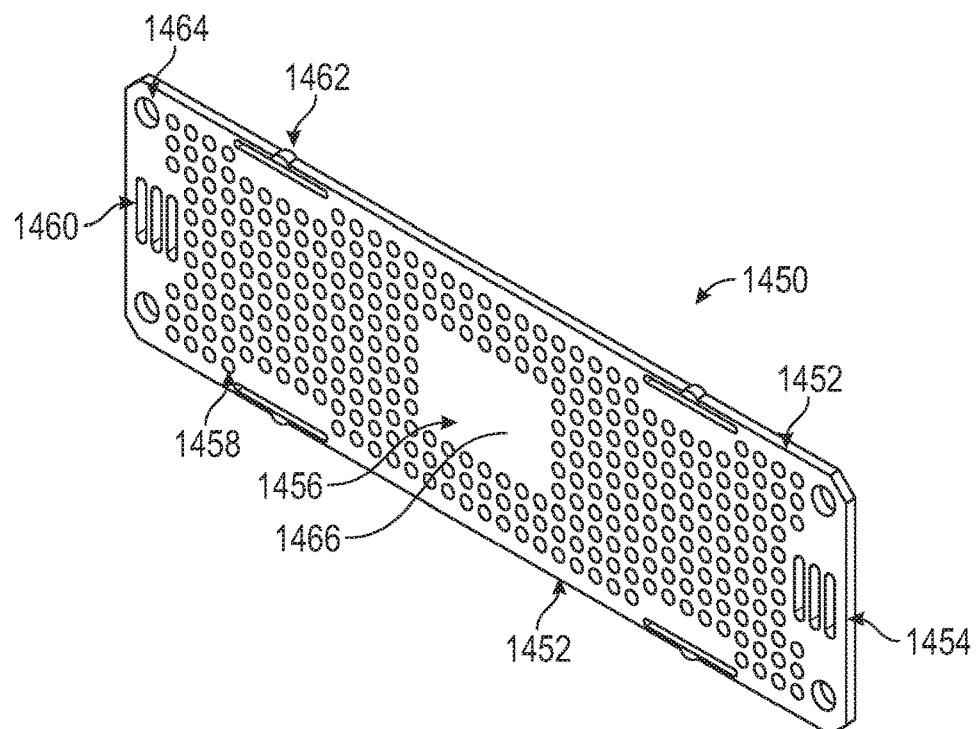
Figure 30A:
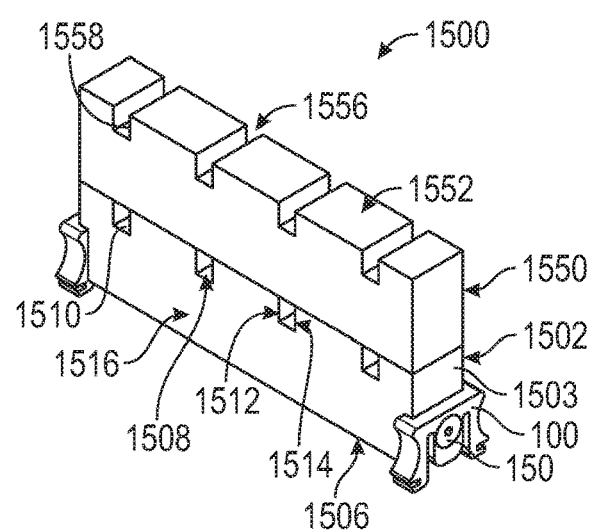
Figure 30B:
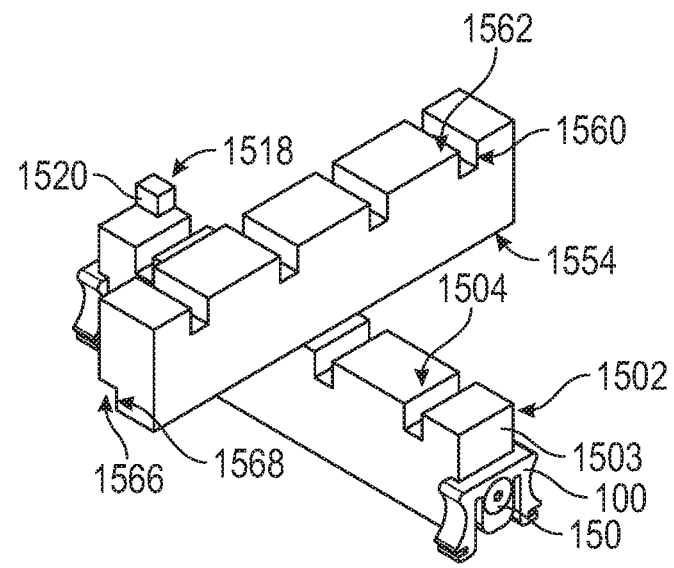
Figure 30C:
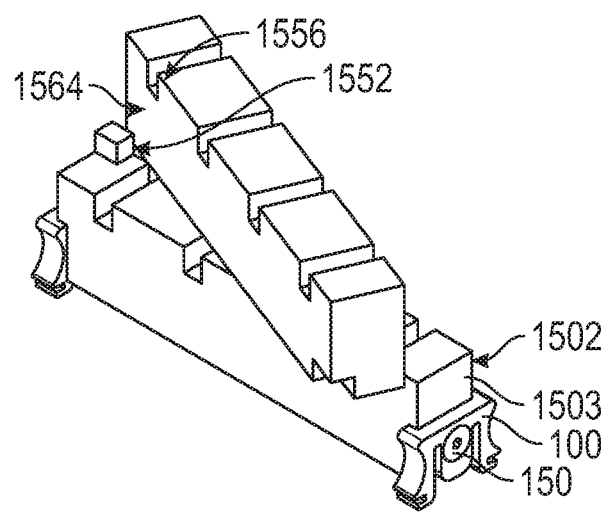

To assist those of ordinary skill in the art in making and using the disclosed assemblies, systems and methods, reference is made to the appended figures, wherein:

FIG. 1 schematically depicts an assembled perspective view of an exemplary modular tray and bracket assembly, according to the present disclosure;

FIG. 2A schematically depicts a bottom view of an exemplary modular tray, according to the present disclosure;

FIG. 2B schematically depicts a side view of an exemplary modular tray, according to the present disclosure;

FIG. 2C schematically depicts a side view of an exemplary modular tray, according to the present disclosure;

FIG. 2D schematically depicts a magnified view of FIG. 2A, according to the present disclosure;

FIG. 3A schematically depicts a front view of an exemplary clip, according to the present disclosure;

FIG. 3B schematically depicts a perspective view of an exemplary clip, according to the present disclosure;

FIG. 4 schematically depicts a perspective view of an exemplary modular bracket assembly, according to the present disclosure;

FIG. 5 schematically depicts a perspective view of an exemplary modular bracket assembly, according to the present disclosure;

FIG. 6A schematically depicts a perspective view of an exemplary modular bracket assembly, according to the present disclosure;

FIGS. 6B and 6C schematically depict a perspective view of an exemplary divider, according to the present disclosure;

FIG. 7 schematically depicts a perspective view of an exemplary modular bracket assembly, according to the present disclosure;

FIG. 8 schematically depicts a perspective view of an exemplary modular bracket assembly, according to the present disclosure;

FIG. 9 schematically depicts a perspective view of an exemplary modular bracket assembly, according to the present disclosure;

FIG. 10 schematically depicts a perspective view of an exemplary modular bracket assembly, according to the present disclosure;

FIG. 11 schematically depicts a perspective view of an exemplary modular bracket assembly, according to the present disclosure;

FIG. 12 schematically depicts a perspective view of an exemplary modular bracket assembly, according to the present disclosure;

FIG. 13 schematically depicts a perspective view of an exemplary modular bracket assembly, according to the present disclosure;

FIG. 14 schematically depicts a perspective view of an exemplary modular bracket assembly, according to the present disclosure;

FIG. 15 schematically depicts a perspective view of an exemplary modular bracket assembly, according to the present disclosure;

FIG. 16A schematically depicts an assembled perspective view of an exemplary modular tray and bracket assembly, according to the present disclosure;

FIG. 16B schematically depicts an assembled perspective view of an exemplary modular tray and bracket assembly, with caddy hidden for ease of viewing assemblies located beneath, according to the present disclosure;

FIG. 16C schematically depicts an assembled perspective view of an exemplary modular tray and cover assembly, with bracket assemblies housed therein, according to the present disclosure;

FIG. 17 schematically depicts a perspective view of an exemplary modular bracket assembly, according to the present disclosure;

FIG. 18 schematically depicts a perspective view of an exemplary modular bracket assembly, according to the present disclosure;

FIG. 19 schematically depicts a perspective view of an exemplary modular bracket assembly, according to the present disclosure;

FIG. 20 schematically depicts a perspective view of an exemplary modular bracket assembly, according to the present disclosure;

FIG. 21 schematically depicts a perspective view of an exemplary modular bracket assembly, according to the present disclosure;

FIG. 22 schematically depicts a perspective view of an exemplary modular bracket assembly, according to the present disclosure;

FIG. 23 schematically depicts a perspective view of an exemplary modular bracket assembly, according to the present disclosure;

FIG. 24 schematically depicts a perspective view of an exemplary modular bracket assembly, according to the present disclosure;

FIG. 25 schematically depicts a perspective view of an exemplary modular bracket assembly, according to the present disclosure;

FIG. 26 schematically depicts a perspective view of an exemplary divider, according to the present disclosure;

FIG. 27A schematically depicts a perspective view of an exemplary modular caddy assembly, according to the present disclosure;

FIG. 27B schematically depicts a perspective view of an exemplary caddy, according to the present disclosure;

FIG. 28A schematically depicts a perspective view of an exemplary modular caddy assembly, according to the present disclosure;

FIG. 28B schematically depicts a perspective view of an exemplary caddy, according to the present disclosure;

FIG. 29 schematically depicts a perspective view of an exemplary caddy cover, according to the present disclosure;

FIG. 30A schematically depicts a perspective view of an exemplary swivel modular bracket assembly, in the closed position, according to the present disclosure;

FIG. 30B schematically depicts a perspective view of an exemplary swivel modular bracket assembly, in the load/unload position, according to the present disclosure; and FIG. 30C schematically depicts a perspective view of an exemplary swivel modular bracket assembly, in the removal/install position, according to the present disclosure.

DETAILED DESCRIPTION OF DISCLOSURE

The exemplary embodiments disclosed herein are illustrative of advantageous mounting assemblies (e.g., assemblies/devices for detachable retention of reusable medical devices during the perioperative process and/or during the central sterile processing process), and systems of the present disclosure and methods/techniques thereof. It should be understood, however, that the disclosed embodiments are merely illustrative of the present disclosure, which may be embodied in various forms. Therefore, details disclosed herein with reference to exemplary assemblies/fabrication methods and associated processes/techniques of assembly and use are not to be interpreted as limiting, but merely as the basis for teaching one skilled in the art how to make and use the advantageous assemblies/systems of the present disclosure.

The present disclosure provides an advantageous assembly for detachably retaining reusable medical devices and other devices relative to a tray. In particular, the present disclosure is directed to systems/methods for detachably retaining reusable medical devices and other instruments during the perioperative process and/or during the central sterile processing process. Even more particularly, exemplary assemblies are disclosed that include a tray with at least one modular bracket assembly mounted directly or indirectly thereto, for detachable retention of reusable medical devices and/or instruments to facilitate use/exposure during the perioperative process and/or during the central sterile processing process.

In exemplary embodiments, the present disclosure provides an advantageous tray and bracket assembly that is configured and adapted to promote modularity and withstand the harsh environment of the central sterile processing process. Exemplary modular bracket assemblies of the present disclosure may be removed and relocated relative to a tray without additional fasteners or components. The disclosed tray and bracket assemblies may further provide identification features to correctly associate cataloged reusable medical devices to identified trays.

Referring now to the drawings, like parts are marked throughout the specification and drawings with the same reference numerals, respectively. Drawing figures are not necessarily to scale and in certain views, parts may have been exaggerated or removed for purposes of clarity.

With reference to FIG. 1, assembly 10 advantageously depicts a potential layout of various modular brackets 200, 250, 300, 350, 400, 450 mounted in relation to tray 12. The interface between modular brackets 200, 250, 300, 350, 400, 450 and tray 12 will be discussed in more detail below. Of note, although assembly 10 depicts a layout of various modular brackets 200, 250, 300, 350, 400, 450, the layout is merely illustrative of one potential surgical procedure and does not limit the scope of this disclosure. It may be appreciated that although several modular brackets 200, 250, 300, 350, 400, 450 are depicted in FIG. 1 that additional designs, as depicted in FIGS. 10-15 and 17-30 may further be incorporated without departing from the spirit/scope of this disclosure. Furthermore, the quantity and placement of modular brackets 200, 250, 300, 350, 400, 450 and those brackets depicted in FIGS. 10-15 and 17-30 may vary without departing from the spirit/scope of this disclosure.

With reference to FIG. 1 in view of FIG. 2, tray 12 includes base 14 and sidewalls 16, 18. Sidewalls 16, 18 extend perpendicularly from base 14 thereby defining inside volume 20 of tray 12. Inside volume 20 may vary depending on the dimensions of tray 12. Any dimensions discussed in this disclosure are merely for facilitating discussion and are not meant to be limiting. Sidewalls 16, 18 may be fabricated with base 14 or may be separate components that are directly or indirectly attached to base 14. Sidewalls may be at a height that is taller than modular bracket assemblies installed within tray 12. Base 14 may further include features 32 (e.g., feet) that may raise base 14 some distance away from a working surface. The quantity of feet 32 may vary depending on the intended design, but enough feet 32 should be used to ensure assembly 10 is even and steady. Feet 32 may be fabricated with base 14 or may be separate components that are directly or indirectly attached to base 14. In one example, feet 32 are installed beneath base 14 by a fastener (e.g., screw, pin, rivet, etc.) or other conventional attachment methods (e.g., welding).

Base 14, sidewalls 16, 18, and feet 32 may be fabricated from a material selected from metal, silicone, plastic, as will be apparent to those skilled in the art. Base 14, sidewalls 16, 18, and feet 32 may be at least partially fabricated from a thermoplastic material, e.g., Radel® (Solvay S.A., Brussels, Belgium), Tecapro® (Ensinger GmbH, Nufringen, Germany), and Propylux® (Westlake Plastics, Lenni, Pa.) materials. For those applications where tray 12 will be exposed to harsh conditions, e.g., an autoclave, materials that can withstand increased heat, humidity, and pressure should be used. However, for those materials that cannot withstand those conditions, a coating should be applied, e.g., anodized coating on metal surfaces. Sidewalls 16, 18 may be attached using conventional attachment methods that are consistent with the material of base 14 and sidewalls 16, 18, e.g., welding, mechanical attachment, adhesives, fasteners, or a combination thereof.

Sidewalls 16, 18 may be substantially planar or may further include feature(s) that cause sidewalls 16, 18 to be nonplanar. The noted feature(s) may be fabricated within or associated with sidewalls 16, 18 and may extend outwardly or inwardly of inside volume 20 of tray 12. In an exemplary embodiment, tray 12 includes feature 22, located on sidewall 18, which includes extension wall 24 and surface 26. Feature 22 further includes concentric opposing holes 28 located on extension wall 24 for retention of a handle (not shown). In another embodiment, feature 22 may include a handle integrated within one or both sidewalls 16, 18. Surface 26 may provide attachment of a clasp mechanism for retention of the cover, as shown in FIG. 16. However, when surface 26 does not include a clasp mechanism, surface 26 may further include identifying information to distinguish each tray 12. The information may include surgery number, patient name, reusable medical devices included within tray 12, hospital name, doctor name, among others, as will be known to one skilled in the art.

In yet another exemplary embodiment, tray 12 may further include features for stacking additional trays 12. Trays 12 may be stacked so that each base 14 is parallel with each base 14 above or below. The disclosed features may be incorporated within sidewalls 16, 18. For example, tabs (not shown) may be incorporated in sidewalls 16, 18 for engagement with base 14 of tray 12 stacked above. Specifically, tabs (not shown) may engage with perforations 30 of base 14. Further, when two or more trays 12 are stacked, with the lowest tray referenced as "A" and the tray above referenced as "B", and so on (C, D, . . . X), base 14 of tray B may be used as the cover of tray A, and so on for each stacked tray. The top tray X may have a cover, as described below.

Tray 12 may further include a plurality of perforations 30, as mentioned above. Perforations 30 may be located on base 14, sidewalls 16, 18, and/or cover (not shown). In exemplary embodiments, perforations are rectangular (e.g., square) in geometry. Perforations 30 may be used to expose the contents of tray 12 to perioperative and central sterile processing process and/or for retention of bracket assemblies 200, 250, 300, 350, 400, 450. However, perforations 30 may have additional uses without departing from the spirit/scope of this disclosure. Perforations 30 may further be aligned in a grid-based pattern to facilitate ease of bracket positioning, wherein perforations 30 may be of even distance between adjacent perforations 30. In an exemplary embodiment, a plurality of perforations 30 are square in shape and are located on base 14 and sidewalls 16, 18, in a grid-based pattern. Such grid-based pattern enables consistent and easily locatable positions for modular bracket assemblies, as discussed below.

Tray 12 may further include unique characters, e.g., alphanumeric characters, to signify horizontal and vertical perforations 30 for ease of bracket positioning. In one example, horizontal perforations 30 may be referenced by letters (e.g., A, B, C . . . etc.) and vertical perforations 30 may be referenced by numbers (e.g., 1, 2, 3 . . . etc.). In another example, horizontal perforations 30 may be referenced by numbers (e.g., 1, 2, 3 . . . etc.) and vertical perforations 30 may be referenced by letters (e.g., A, B, C . . . etc.). Regardless of character choice, horizontal and vertical perforations 30 may be the same or different character type, thereby creating a coordinate system for pinpointing a specific perforation, or series of perforations, on a grid. In doing so, the location of one or more brackets 200, 250, 300, 350, 400, 450 will easily be determined. The above-described characters may be inscribed on base 14, adjacent to the outermost horizontal and vertical row/column of perforations 30 of tray 12 (or sidewalls 16, 18, or cover). Such positioning capabilities may be useful for a medical professional to quickly locate a reusable medical device during surgery and/or during inventory storage (and for access/location thereof).

Assembly 10 may further include a cover (not shown) to encase the components housed within tray 12. In one example, the disclosed cover may be a separate component of tray 12 that is entirely removable and is in contact with sidewalls 16, 18. In another example, the disclosed cover is hingedly attached to tray 12 such that the contents housed within tray 12 are accessible when said cover is open, but, when open, the cover continues to remain at least partially in contact with tray 12. The disclosed cover may be removable from tray 12 by removing at least a portion of the hinges. The disclosed cover may include perforations, as described above, and may further include brackets for retention of reusable medical devices. In an exemplary embodiment, the disclosed cover includes features that enable stacking of additional trays. Features may be incorporated into the exterior of cover (not shown) that capture feet 32, for example, indentations or clips. In another exemplary embodiment, cover 13, as depicted in FIG. 16C, may be used with assembly 10.

As mentioned above, modular bracket assembly 200, 250, 300, 350, 400, 450, among others, as discussed below, may be directly or indirectly mounted in relation to tray 12. In an exemplary embodiment, modular bracket assembly 200, 250, 300, 350, 400, 450, among others, as discussed below, may be mounted in relation to perforations 30 of base 14. The disclosed attachment may be accomplished, for example, by clip 100, depicted in FIG. 3, which may be incorporated with any modular bracket, disclosed herein, or other bracket design.

With reference to FIGS. 3A and 3B, at least one clip 100 may be attached to the disclosed modular bracket to semi-permanently attach the disclosed modular bracket directly or indirectly to tray 12, discussed in more detail below. Clip 100 includes body 102 and two symmetrically opposed arms 104, located on either side of body 102 and separated by at least one channel. Arms 104 define an elongated axis. Arms 104 may be at least partially rigid and/or at least partially deflectable. Surface (i.e., bridge) 106 connects arm 104 to body 102 by way of shoulder 107. Bridge 106 may be at least partially rigid and/or at least partially deflectable.

Located above arm base 108 is cavity (i.e., mounting structure) 115, which includes interface features that attach directly or indirectly to an edge of perforation 30. The disclosed interface features of cavity 115 may include back face 114, upper extension 116, and lower extension 118, which collectively form cavity 115. Upper extension 116 and lower extension 118 may extend transversely relative to the elongated axis of arm 104 to form cavity 115. Upper extension 116 and lower extension 118 may be parallel to one another. Upper extension 116 and lower extension 118 may extend substantially perpendicularly from arm 104. In relation to back face 114, the length of lower extension 118 may be shorter than the length of upper extension 116, as depicted. Lower extension 118 having a shorter length enables an easier installation and removal from perforation 30 without sacrificing clip 100 engagement. However, in another embodiment, upper extension 116 and lower extension 118 may have similarly dimensioned lengths. Cavity 115 may be shaped in a substantially U-shaped configuration, as depicted. Additional cavity 115 shapes may be utilized (e.g., quadrilateral).

In exemplary operation, at least a portion of cavity 115 captures a portion of at least one edge of perforation 30. To ensure clip 100 does not shift after installation with tray 12, back face 114 is under spring load in contact with an edge of perforation 30. Furthermore, upper extension 116 and lower extension 118 may be in close proximity to tray 12. Particularly, upper extension 116 and lower extension 118 may at least partially engage with at least one edge surface of perforation 30. Even more particularly, upper extension 116 may at least partially engage with an upper face of at least one edge of perforation 30 and lower extension 118 may at least partially engage with a lower face of at least one edge of perforation 30.

In one example, by simultaneously compressing arms 104, such that arms 104, surface 106, and/or shoulder 107 at least partially deflect, face 112 moves closer to body 102 and the distance between back faces 114 is reduced. Reduction of the distance between back faces 114 enables cavity 115 to be engaged with an edge of the respective perforations 30. Once arms 104 are released into their relaxed position, back face 114 will be in contact with a desired engagement surface on the respective perforation 30. Particularly, since the resting distance between back faces 114 is greater than the distance between the engagement surfaces (e.g., edge of perforation 30), arms 104 remain in slight compression and therefore apply a spring load to the engagement surface of the respective perforation 30. In another example, by individually compressing arms 104, such that arms 104, surface 106, and/or shoulder 107 at least partially deflect, one cavity 115 may be engaged with the respective perforation 30. Upon engagement of one cavity 115, second cavity 115 may be engaged with perforation 30. Aside from the method to engage clip 100 with tray 12 (e.g., individual arm compression or simultaneous arm compression), the engagement with perforation 30 is substantially similar Therefore, arms 104 apply a spring load to the desired engagement surface on the respective perforation 30. Of note, attachment is not to be limited to tray 12; rather, attachment may further be accomplished with sidewalls 16, 18 and cover (not shown). For purposes of the present disclosure, when one of tray 12, sidewalls 16, 18, and/or cover are mentioned, the others not mentioned are included, unless otherwise stated.

In an exemplary embodiment, arms 104 may include a semi-circular feature 110 located on the outside surface of arm 104 that is opposite surface 112. Semi-circular feature 110 may provide a specific location for the user to place their fingers to assist in compressing arms 104 for insertion or removal from tray 12.

With reference to FIGS. 4-15 and 17-30, various bracket design assemblies may utilize at least one clip 100, described above, for direct or indirect attachment to tray 12. In an exemplary embodiment, two clips 100 may be attached to the ends of the disclosed brackets, discussed in more detail below. Although depicted as a separate component, clip 100 (or clips 100) may be integrally fabricated with any one of the disclosed bracket assemblies, i.e., as an integral component. For example, the integral component may be fabricated as a single component through a variety of manufacturing methods, e.g., molding, casting, extruding, among other methods. Clip 100 may be associated with a bracket through at least one body 102, arms 104, and bridge 106. Bracket assemblies depicted in FIGS. 4-15 and FIGS. 17-30 may further include at least one reusable medical device/instrument therein. Several bracket designs may include at least one attachment feature to capture at least a portion of the exterior surface of at least one reusable medical device/instrument. In an exemplary embodiment, the attachment feature may retain the exterior surface of the reusable medical device/instrument using friction.

The disclosed clip and brackets may be fabricated from a material that is impervious to the harsh conditions of central sterile processing processes. However, materials that are not impervious to the conditions of central sterile processing processes may be coated so as to make them resistant, i.e., able to withstand sterilization conditions. For example, the disclosed clip and brackets may be fabricated from plastic, silicone, or metal. In an exemplary embodiment, the brackets may be fabricated from a thermoplastic material, e.g., Radel® (Solvay S.A., Brussels, Belgium), Tecapro® (Ensinger GmbH, Nufringen, Germany), and Propylux® (Westlake Plastics, Lenni, Pa.) materials. Components fabricated from metal may be anodized to withstand sterilization conditions.

Brackets may be color-coded and/or include other indicia so as to quickly notify a user specific information about the reusable medical device/instrument. In one example, since a surgery may include several trays of surgical reusable medical devices, a color may signify a specific step in the surgical process, e.g., blue refers to the first step in a surgery, green refers to the second, and so on. In another example, the color of the bracket may refer to a specific reusable medical device, e.g., pink refers to a driver, yellow refers to a scissors, and so on. For purposes of the foregoing color-coded examples, alternative indicia may be employed, e.g., numerical indicia imprinted on the brackets, coded-protuberances or other physical indicia formed on or mounted to the brackets, or the like.

In another exemplary embodiment, each bracket may include at least one feature, e.g., embedded electrical connection, to track a reusable medical device/instrument and notify a user of an event. In one example, when a conductive portion (or feature) of a reusable medical device/instrument makes contact with the embedded electrical connection, the circuit may be completed and information specific to that reusable medical device/instrument may be transferred to a user. For example, a reusable medical device/instrument may have specific electrical characteristics such that a disclosed bracket may be adapted to track the presence/absence of the reusable medical device/instrument. In such case, when the reusable medical device/instrument is removed from the bracket, a signal may be sent to a processor/recording software to notify that such reusable medical device/instrument has been removed. The disclosed tracking functionality may assist in compliance with Unique Device Identification ("UDI") protocols, currently in development with the U.S. Food & Drug Administration. In another example, the disclosed bracket may include inscribed identification reading capabilities, e.g., QR code or barcode, so as to "read" the presence of a reusable medical device/instrument that is outfitted with an inscribed identification feature. The disclosed inscribed identification feature may include information about a surgery, a patient, a hospital, and the like, among other important identification information.

With specific reference to FIG. 4, modular bracket assembly 200 includes bracket 202 and clip 100. Clip 100 may be in direct or indirect contact with bracket 202. Attachment between clip 100 and bracket 202 may be accomplished by permanent or semi-permanent fastener 150, e.g., rivet, screw/bolt, nail, pin, adhesive, weld, etc. However, attachment between clip 100 and bracket 202 is not limited to fastener 150. For example, clip 100 and bracket 202 may be fabricated as one part or bracket 202 and/or clip 100 may include connecting features to interface the other, without additional fasteners. In an exemplary embodiment, clip 100 is attached to bracket 202 in an appropriately sized cutout located on end surface 203 of bracket 202. However, clip 100 may also be attached to surface 203 without a cutout. Clip 100 may further be attached to bottom surface 206. The above-mentioned clip 100 location(s) and attachment mechanism(s) is/are merely illustrative and are not intended to be limiting.

Bracket 202 features top surface 204 and bottom surface 206 with various sized U-shaped or partially U-shaped cavities 208, 210 fabricated therein. U-shaped cavities 208, 210, i.e., attachment feature, may capture the exterior surface of a reusable medical device for retention to tray 12. U-shaped cavity 208 may be used to capture the handle of a reusable medical device (not shown). Conversely, U-shaped cavity 210 may be used to capture the tool portion of a reusable medical device (not shown). However, additional/alternative attachment configurations may be incorporated. In an exemplary embodiment, pairs of modular bracket assemblies 200 may be situated opposite each other on tray 12 so as one modular bracket assembly 200 captures the handle of a reusable medical device, the opposing modular bracket assembly 200 captures the tool portion of the same reusable medical device.

With specific reference to FIG. 5, modular bracket assembly 250 includes bracket 252 and clip 100. Clip 100 may be in direct or indirect contact with bracket 252. Attachment between clip 100 and bracket 252 may be accomplished by permanent or semi-permanent fastener 150, e.g., rivet, screw/bolt, nail, pin, adhesive, weld, etc. However, attachment between clip 100 and bracket 252 is not limited to fastener 150. For example, clip 100 and bracket 252 may be fabricated as one part or bracket 252 and/or clip 100 may include connecting features to interface the other, without additional fasteners. In an exemplary embodiment, clip 100 is attached to bracket 252 in an appropriately sized cutout located on end surface 253 of bracket 252. However, clip 100 may also be attached to surface 253 without a cutout. Clip 100 may further be attached to bottom surface 256. The above-mentioned clip 100 location(s) and attachment mechanism(s) is/are merely illustrative and are not intended to be limiting.

Bracket 252 includes top surface 254, bottom surface 256, and ledge 258. Extending between ledge 258 and top surface 254 are features for retention of reusable medical device(s)/instrument(s) and/or additional bracketry (e.g., partitions or dividers). Specifically, slot 262 extends perpendicularly from ledge 258. Axially located above slot 262, but beneath top surface 254, is partial U-shaped cavity 260. In an exemplary embodiment, slot 262 transitions into axially located partial U-shaped cavity 260. However, the featured design and location are merely illustrative and may include several designs at various locations along bracket 252.

In yet another example, not shown, features may extend perpendicularly inward from face 264 so as to provide a location for insertion of a divider. The disclosed divider may provide for another level of reusable medical device/instrument storage. In an exemplary embodiment, a perpendicular slot may be located at or around the transition point between partial U-shaped cavity 260 and slot 262. In doing so, reusable medical devices may be inserted into slot 262 and rested on ledge 258, and a second level of reusable medical devices may be inserted into partial U-shaped cavity 260 and rested on divider (not shown).

With further reference to FIG. 5 in view of FIGS. 6A-6C, modular box assembly 300 includes modular bracket assembly 250 and dividers/partitions 302, 312 (referred to as "dividers" herein below). In exemplary operation, at least two modular bracket assemblies 250 are connected by at least two dividers 302. Divider 302 includes at least two connecting cavities 304 that interface with slot 262 of bracket 252. Surface 306 of divider 302 may interface with ledge 258 of bracket 252 to provide additional stability and to ensure divider 302 is fully engaged with bracket 252. Further, at least one divider 312 connects the at least two dividers 302. Specifically, divider 302 further includes cavity 308 which interfaces with cavity 314 of divider 312. Surface 310 of divider 302 may contact surface 316 of divider 312 to signify to the user that both dividers 302, 312 are fully assembled.

In an exemplary embodiment, two modular bracket assemblies 250 are connected by two dividers 302. Divider 302 includes two connecting cavities 304 that interface with slot 262 of bracket 252. Surface 306 of divider 302 may interface with ledge 258 of bracket 252 to provide additional stability and to ensure divider 302 is fully engaged with bracket 252. Further, cavity 314 of divider 312 interfaces with cavity 308 of dividers 302. Surface 310 of divider 302 may contact surface 316 of divider 312 to signify to the user that both dividers 302, 312 are fully assembled. Accordingly, box assembly 300 includes two storage cavities 320, defined by dividers 302, 312 and bracket assembly 252.

As stated above, box assembly is modular and may accommodate several box designs, including removing divider 312 to form one storage cavity 320. The disclosed box assembly 300 may be in direct or indirect contact with tray 12 through clips 100 included with modular bracket assembly 252. In another example, divider 312 may further include a cutout extending from top surface 318 to the base of box assembly 300 that allows installation of reusable medical devices in partial U-shaped cavity 260 and slot 262 while further including storage cavity 320.

With reference to FIG. 7, modular bracket assembly 350 includes bracket 352 and clip 100. Clip 100 may be in direct or indirect contact with bracket 352. Attachment between clip 100 and bracket 352 may be accomplished by permanent or semi-permanent fastener 150, e.g., rivet, screw/bolt, nail, pin, adhesive, weld, etc. However, attachment between clip 100 and bracket 352 is not limited to fastener 150. For example, clip 100 and bracket 352 may be fabricated as one part or bracket 352 and/or clip 100 may include connecting features to interface the other, without additional fasteners. In an exemplary embodiment, clip 100 is attached to bracket 352 in an appropriately sized cutout located on end surface 353 of bracket 352. However, clip 100 may also be attached to surface 353 without a cutout. Clip 100 may further be attached to bottom surface 356. The above-mentioned clip 100 location(s) and attachment mechanism(s) is/are merely illustrative and are not intended to be limiting.

Bracket 352 includes top surface 354 and bottom surface 356. Extending from top surface 354 towards bottom surface 356 is partial U-shaped cavity 358. Located axially beneath partial U-shaped cavity 358 is slot 360 and semi-circular feature 362. Partial U-shaped cavity 358 and slot 360 may accommodate reusable medical devices and/or additional bracketry (e.g., dividers). Semi-circular feature 362 enables easier installation of circular diameter surgical reusable medical devices, but the present disclosure is not limited by or to such geometry.

In another example, not shown, one or more features may extend perpendicularly inward from face 364 so as to provide a location for insertion of a divider. The disclosed divider may provide for an additional level of reusable medical device/instrument storage. In an exemplary embodiment, a perpendicular slot may be located at or around the transition point between partial U-shaped cavity 358 and slot 360. In doing so, reusable medical devices may be inserted into slot 360 and rested on semi-circular feature 362, and a second level of reusable medical devices may be inserted into partial U-shaped cavity 358 and rested on divider (not shown).

With reference to FIG. 8, modular bracket assembly 400 includes bracket 402 and clip 100. Clip 100 may be in direct or indirect contact with bracket 402. Attachment between clip 100 and bracket 402 may be accomplished by permanent or semi-permanent fastener 150, e.g., rivet, screw/bolt, nail, pin, adhesive, weld, etc. However, attachment between clip 100 and bracket 402 is not limited to fastener 150. For example, clip 100 and bracket 402 may be fabricated as one part or bracket 402 and/or clip 100 may include connecting features to interface the other, without additional fasteners. In an exemplary embodiment, clip 100 is attached to bracket 402 in an appropriately sized cutout located on end surface 403 of bracket 402. However, clip 100 may also be attached to surface 403 without a cutout. Clip 100 may further be attached to bottom surface 408. The above-mentioned clip 100 location(s) and attachment mechanism(s) is/are merely illustrative and are not intended to be limiting.

Bracket 402 includes first top surface 404, second top surface 406, and bottom surface 408. Extending from first top surface 404 towards bottom surface 408 and further defining second top surface 406 is cavity 410. Cavity 410 and base 412 may accommodate reusable medical devices and/or bracketry (e.g., dividers). As depicted, second top surface 406 is shorter in distance from base 412 than first top surface 404. Reduction of second top surface 406 reduces cost by utilizing less material and provides a more compact design. However, bracket 402 is not limited to such design and the height variation, if any, may be altered depending on the intended purpose. Further, although depicted as two cavities 410, additional cavities may be included by merely increasing the size of bracket 402. The disclosed two cavity design is merely illustrative, and is not intended to be limiting for purposes of the present disclosure.

In an exemplary embodiment, cavity sidewalls 414, 416 define a slight angle such that base 412 is smaller in width than the opening of cavity 410. By angling sidewalls 414, 416, larger-sized reusable medical devices and/or bracketry may be incorporated without altering the perimeter dimensions of bracket 402. However, in another example, sidewalls 414, 416 are perpendicular to base 412 such that the width of base 412 and the opening of cavity 410 are complementary. The width of base 412 and the opening of cavity 410 may be altered to accomplish the intended purpose of modular bracket assembly 400. Further, features 418 may assist in inserting reusable medical devices and/or bracketry into cavity 410. The design of such features 418 may include chamfered edges, radiused edges, as well as other geometries.

With reference to FIG. 9, modular bracket assembly 450 includes bracket 452 and clip 100. Clip 100 may be in direct or indirect contact with bracket 452. Attachment between clip 100 and bracket 452 may be accomplished by permanent or semi-permanent fastener 150, e.g., rivet, screw/bolt, nail, pin, adhesive, weld, etc. However, attachment between clip 100 and bracket 452 is not limited to fastener 150. For example, clip 100 and bracket 452 may be fabricated as one part or bracket 452 and/or clip 100 may include connecting features to interface the other, without additional fasteners. In an exemplary embodiment, clip 100 is attached to bracket 452 in an appropriately sized cutout located on end surface 453 of bracket 452. However, clip 100 may also be attached to surface 453 without a cutout. Clip 100 may further be attached to bottom surface 458. The above-mentioned clip 100 location(s) and attachment mechanism(s) is/are merely illustrative and are not intended to be limiting.

Bracket 452 includes first top surface 454, second top surface 456, and bottom surface 458. Extending from first top surface 454 towards bottom surface 458 and further defining second top surface 456 is cavity 460. Cavity 460 and base 462 may accommodate reusable medical devices and/or bracketry (e.g., dividers). As depicted, first top surface 454 and second top surface 456 are at similar heights from base 462. However, as discussed above, bracket 452 is not limited to such design and any height variation may be utilized to accomplish the intended purpose. Further, although depicted as two cavities 460, additional cavities may be included by merely increasing the size of bracket 452. The disclosed two cavity design is merely illustrative and is not intended to be limiting.

In an exemplary embodiment, cavity sidewalls 464, 466 define a slight angle such that base 462 is smaller in width than the opening of cavity 460. By angling sidewalls 464, 466, as described above, larger-sized reusable medical devices and/or bracketry may be incorporated without altering the perimeter dimensions of bracket 452. However, in another example, sidewalls 464, 466 are perpendicular to base 462 such that the width of base 462 and the opening of cavity 460 are complementary. The width of base 462 and the opening of cavity 460 may be altered to accomplish the intended purpose of modular bracket assembly 450. Further, features 468 may assist in inserting reusable medical devices and/or bracketry into cavity 460. The design of such features 468 may include chamfered edges, radiused edges, as well as other geometries.

In another example, not shown, features may extend perpendicularly inward from face 470 so as to provide a location for insertion of a divider. The disclosed divider may provide an additional level of reusable medical device/instrument storage. The disclosed divider may perpendicularly intersect cavity 460 so as to create an additional level of storage. In doing so, reusable medical devices may be inserted into a first level, e.g., the portion below the divider (not shown), and rested on base 462, and also inserted into a second level, e.g., the portion above the divider (not shown), and rested on divider (not shown).

Of note, bracket assemblies 200, 250, 300, 350, 400, 450, as depicted in FIGS. 4-9, may be included within assembly 10 of FIG. 1. However, as mentioned above, the layout of assembly 10 is not limited to only those exemplary bracket assemblies. For example, bracket assemblies 500, 550, 600, 650, 700, 750, as depicted in FIGS. 10-15, although not illustrated in assembly 10, may be included therein without departing from the spirit/scope of this disclosure. Further, some or all of the bracket assemblies of FIGS. 17-30 may be included in assembly 10.

The three modular bracket assemblies 500, 550, 600, as depicted in FIGS. 10-12, are similar in design, but include various-sized cavities. For completeness and ease of understanding, each assembly will be discussed separately. In comparison, the cavity width of modular bracket assemblies 500, 550, 600 increase relative to the modular bracket assembly number, with modular bracket assembly 500 having the smallest cavity width.

With reference to FIG. 10, modular bracket assembly 500 includes bracket 502 and clip 100. Clip 100 may be in direct or indirect contact with bracket 502. Attachment between clip 100 and bracket 502 may be accomplished by permanent or semi-permanent fastener 150, e.g., rivet, screw/bolt, nail, pin, adhesive, weld, etc. However, attachment between clip 100 and bracket 502 is not limited to fastener 150. For example, clip 100 and bracket 502 may be fabricated as one part or bracket 502 and/or clip 100 may include connecting features to interface the other, without additional fasteners. In an exemplary embodiment, clip 100 is attached to bracket 502 in an appropriately sized cutout located on end surface 503 of bracket 502. However, clip 100 may also be attached to surface 503 without a cutout. Clip 100 may further be attached to bottom surface 506. The above-mentioned clip 100 location(s) and attachment mechanism(s) is/are merely illustrative and are not intended to be limiting.

Bracket 502 includes top surface 504, bottom surface 506, and ledge 508. Extending from top surface 504 towards ledge 508 is U-shaped cavity 510. Cavity 510 and base 512 may accommodate reusable medical devices and/or bracketry (e.g., dividers). Cavity 510 further includes sidewalls 514, 516, which define a cavity width. As is evident from FIGS. 10-12, cavity 510 is not limited to a specific width; rather, width variation may depend on the intended purpose of modular bracket assembly 500. Further, although depicted as one cavity 510, additional cavities may be included by merely increasing the size of bracket 502. Accordingly, the disclosed single cavity design is merely illustrative, and is not intended to be limiting.

In an exemplary embodiment, cavity sidewalls 514, 516 are substantially perpendicular to ledge 508. Such orientation provides firm boundaries for constraint of reusable medical devices and/or bracketry. However, as discussed above, cavity sidewalls 514, 516 may define a slight angle such that base 512 is smaller in width than the opening of cavity 510. By angling sidewalls 514, 516, as described above, larger-sized reusable medical devices and/or bracketry may be incorporated without altering the perimeter dimensions of bracket 502. The width of base 512 and the opening of cavity 510 may be altered to accomplish the intended purpose of modular bracket assembly 500. Further, features (not shown) may assist in inserting reusable medical devices and/or bracketry into cavity 510. The design of such features (not shown) may include chamfered edges, radiused edges, as well as other geometries.

In another example, not shown, features may extend perpendicularly inward from face 518 so as to provide a location for insertion of a divider. The disclosed divider may provide an additional level of reusable medical device/instrument storage. The disclosed divider may perpendicularly intersect cavity 510 so as to create an additional level of storage. In such exemplary implementations, reusable medical devices may be inserted into a first level, e.g., the portion below the divider (not shown), and rested on base 512, and also inserted into a second level, e.g., the portion above the divider (not shown), and rested on divider (not shown).

With regards to FIG. 11, modular bracket assembly 550 includes bracket 552 and clip 100. Clip 100 may be in direct or indirect contact with bracket 552. Attachment between clip 100 and bracket 552 may be accomplished by permanent or semi-permanent fastener 150, e.g., rivet, screw/bolt, nail, pin, adhesive, weld, etc. However, attachment between clip 100 and bracket 552 is not limited to fastener 150. For example, clip 100 and bracket 552 may be fabricated as one part or bracket 552 and/or clip 100 may include connecting features to interface the other, without additional fasteners. In an exemplary embodiment, clip 100 is attached to bracket 552 in an appropriately sized cutout located on end surface 553 of bracket 552. However, clip 100 may also be attached to surface 553 without a cutout. Clip 100 may further be attached to bottom surface 556. The above-mentioned clip 100 location(s) and attachment mechanism(s) is/are merely illustrative and are not intended to be limiting.

Bracket 552 includes top surface 554, bottom surface 556, and ledge 558. Extending from top surface 554 towards ledge 558 is U-shaped cavity 560. Cavity 560 and base 562 may accommodate reusable medical devices and/or bracketry (e.g., dividers). Cavity 560 further includes sidewalls 564, 566, which define a cavity width. As is evident from FIGS. 10-12, cavity 560 is not limited to a specific width; rather, width variation may depend on the intended purpose of modular bracket assembly 550. Further, although depicted as one cavity 560, additional cavities may be included by merely increasing the size of bracket 552. The disclosed single cavity design is merely illustrative and is not intended to be limiting.

In an exemplary embodiment, cavity sidewalls 564, 566 are substantially perpendicular to ledge 558. Such orientation provides firm boundaries for constraint of surgical reusable medical devices and/or bracketry. However, as discussed above, cavity sidewalls 564, 566 may define a slight angle such that base 562 is smaller in width than the opening of cavity 560. By angling sidewalls 564, 566, as described above, larger-sized reusable medical devices and/or bracketry may be incorporated without altering the perimeter dimensions of bracket 552. The width of base 562 and the opening of cavity 560 may be altered to accomplish the intended purpose of modular bracket assembly 550. Further, features (not shown) may assist in inserting reusable medical devices and/or bracketry into cavity 560. The design of such features (not shown) may include chamfered edges, radiused edges, as well as other geometries.

In another example, not shown, features may extend perpendicularly inward from face 568 so as to provide a location for insertion of a divider. The disclosed divider may provide an additional level of reusable medical device/instrument storage. The disclosed divider may perpendicularly intersect cavity 560 so as to create an additional level of storage. In such exemplary implementation, reusable medical devices may be inserted into a first level, e.g., the portion below the divider (not shown), and rested on base 562, and also inserted into a second level, e.g., the portion above the divider (not shown), and rested on divider (not shown).

With regards to FIG. 12, modular bracket assembly 600 includes bracket 602 and clip 100. Clip 100 may be in direct or indirect contact with bracket 602. Attachment between clip 100 and bracket 602 may be accomplished by permanent or semi-permanent fastener 150, e.g., rivet, screw/bolt, nail, pin, adhesive, weld, etc. However, attachment between clip 100 and bracket 602 is not limited to fastener 150. For example, clip 100 and bracket 602 may be fabricated as one part or bracket 602 and/or clip 100 may include connecting features to interface the other, without additional fasteners. In an exemplary embodiment, clip 100 is attached to bracket 602 in an appropriately sized cutout located on end surface 603 of bracket 602. However, clip 100 may also be attached to surface 603 without a cutout. Clip 100 may further be attached to bottom surface 606. The above-mentioned clip 100 location(s) and attachment mechanism(s) is/are merely illustrative and are not intended to be limiting.

Bracket 602 includes top surface 604, bottom surface 606, and ledge 608. Extending from top surface 604 towards ledge 608 is U-shaped cavity 610. Cavity 610 and base 612 may accommodate reusable medical devices and/or bracketry (e.g., dividers). Cavity 610 further includes sidewalls 614, 616, which define a cavity width. As is evident from FIGS. 10-12, cavity 610 is not limited to a specific width; rather, width variation may depend on the intended purpose of modular bracket assembly 600. Further, although depicted as one cavity 610, additional cavities may be included by merely increasing the size of bracket 602. The disclosed single cavity design is merely illustrative and is not intended to be limiting.

In an exemplary embodiment, cavity sidewalls 614, 616 are substantially perpendicular to ledge 608. Such orientation provides firm boundaries for constraint of reusable medical devices and/or bracketry. However, as discussed above, cavity sidewalls 614, 616 may define a slight angle such that base 612 is smaller in width than the opening of cavity 610. By angling sidewalls 614, 616, as described above, larger-sized reusable medical devices and/or bracketry may be incorporated without altering the perimeter dimensions of bracket 602. The width of base 612 and the opening of cavity 610 may be altered to accomplish the intended purpose of modular bracket assembly 600. Further, features (not shown) may assist in inserting reusable medical devices and/or bracketry into cavity 610. The design of such features (not shown) may include chamfered edges, radiused edges, as well as other geometries.

In another example, not shown, features may extend perpendicularly inward from face 618 so as to provide a location for insertion of a divider. The disclosed divider may provide an additional level of reusable medical device/instrument storage. The disclosed divider may perpendicularly intersect cavity 610 so as to create an additional level of storage. In such exemplary embodiment, reusable medical devices may be inserted into a first level, e.g., the portion below the divider (not shown), and rested on base 612, and also inserted into a second level, e.g., the portion above the divider (not shown), and rested on divider (not shown).

With regards to FIG. 13, modular bracket assembly 650 includes bracket 652 and clip 100. Clip 100 may be in direct or indirect contact with bracket 652. Attachment between clip 100 and bracket 652 may be accomplished by permanent or semi-permanent fastener 150, e.g., rivet, screw/bolt, nail, pin, adhesive, weld, etc. However, attachment between clip 100 and bracket 652 is not limited to fastener 150. For example, clip 100 and bracket 652 may be fabricated as one part or bracket 652 and/or clip 100 may include connecting features to interface the other, without additional fasteners. In an exemplary embodiment, clip 100 is attached to bracket 652 in an appropriately sized cutout located on end surface 653 of bracket 652. However, clip 100 may also be attached to surface 653 without a cutout. Clip 100 may further be attached to bottom surface 656. The above-mentioned clip 100 location(s) and attachment mechanism(s) is/are merely illustrative and are not intended to be limiting.

Bracket 652 includes top surface 654, bottom surface 656, and ledge 658. Extending from top surface 654 towards ledge 658 are two slots 668 and a substantially U-shaped cavity 660. In an exemplary embodiment, in viewing bracket 652 from face 676, slots 668 are located on either side of U-shaped cavity 660. Slots 668 and cavity 660 may accommodate reusable medical devices and/or bracketry (e.g., dividers).

Cavity 660 further includes base 662 and sidewalls 664, 666, which define the height and width of cavity 660, respectively. However, as discussed above, cavity 660 is not limited to a specific height or width; rather, height/width variation may depend on the intended purpose of modular bracket assembly 650. Further, although depicted as one cavity 660, additional cavities may be included by merely increasing the size of bracket 652. The disclosed single cavity design is merely illustrative and is not intended to be limiting.

Slots 668 further include base 670 and sidewalls 672, 674, which define the height and width of slot 668, respectively. However, as discussed above, slot 668 is not limited to a specific height or width; rather, height/width dimensions may be altered to satisfy the intended purpose of modular bracket assembly 650. Further, although depicted as two slots 668, additional slots may be included by merely increasing the size of bracket 652. The disclosed two slot design is merely illustrative and is not intended to be limiting. Indeed, designs that include more or less than two slots may be utilized.

In an exemplary embodiment, cavity sidewalls 664, 666 are substantially perpendicular to ledge 658. Further, slot sidewalls 672, 674 are substantially perpendicular to ledge 658, discussed in more detail below. Such orientation provides firm boundaries for constraint of reusable medical devices and/or bracketry. However, as discussed above, cavity sidewalls 664, 666 may define a slight angle such that base 662 is smaller in width than the opening of cavity 660. By angling sidewalls 664, 666, as described above, larger-sized reusable medical devices and/or bracketry may be incorporated without altering the perimeter dimensions of bracket 652. The width of base 662 and the opening of cavity 660 may be altered to satisfy the intended purpose of modular bracket assembly 650. Further, features (not shown) may assist in inserting reusable medical devices and/or bracketry into cavity 660. The design of such features (not shown) may include chamfered edges, radiused edges, as well as other geometries.

As mentioned above, slot sidewalls 672, 674 are substantially perpendicular to ledge 658. Such orientation provides firm boundaries for constraint of reusable medical devices and/or bracketry. However, as discussed above, slot sidewalls 672, 674 may define a slight angle such that base 670 is smaller in width than the opening of slot 668. By angling slot sidewalls 672, 674, as described above, larger-sized reusable medical devices and/or bracketry may be incorporated without altering the perimeter dimensions of bracket 652. The width of base 670 and the opening of slot 668 may be altered to satisfy the intended purpose of modular bracket assembly 650. Further, features 678 may assist in inserting reusable medical devices and/or bracketry into slot 668. The design of such features 678 may include chamfered edges, radiused edges, as well as other geometries.

In another example, not shown, features may extend perpendicularly inward from face 676 so as to provide a location for insertion of a divider. The disclosed divider may provide an additional level of reusable medical device/instrument storage. The disclosed divider may perpendicularly intersect cavity 660 and slots 668 so as to create an additional level of storage. In such exemplary implementation, reusable medical devices may be inserted into a first level, e.g., the portion below the divider (not shown), and rested on base 662, 670, and also inserted into a second level, e.g., the portion above the divider (not shown), and rested on divider (not shown).

With regards to FIG. 14, modular bracket assembly 700 includes bracket 702 and clip 100. Clip 100 may be in direct or indirect contact with bracket 702. Attachment between clip 100 and bracket 702 may be accomplished by permanent or semi-permanent fastener 150, e.g., rivet, screw/bolt, nail, pin, adhesive, weld, etc. However, attachment between clip 100 and bracket 702 is not limited to fastener 150. For example, clip 100 and bracket 702 may be fabricated as one part or bracket 702 and/or clip 100 may include connecting features to interface the other, without additional fasteners. In an exemplary embodiment, clip 100 is attached to bracket 702 in an appropriately sized cutout located on end surface 703 of bracket 702. However, clip 100 may also be attached to surface 703 without a cutout. Clip 100 may further be attached to bottom surface 706. The above-mentioned clip 100 location(s) and attachment mechanism(s) is/are merely illustrative and are not intended to be limiting.

Bracket 702 includes top surface 704 and bottom surface 706. Extending from top surface 704 towards bottom surface 706 is slot 708 which transitions into two substantially U-shaped cavities 714, 716. U-shaped cavities 714, 716 are situated perpendicular to each other. However, such orientation is merely illustrative of one potential layout and such layout is not intended to be limiting. Also included are two substantially U-shaped cavities 718. In an exemplary embodiment, in viewing bracket 702 from face 726, U-shaped cavities 718 are symmetrically located on either side of slot 708. U-shaped cavities 714, 716, 718 and slot 708 may accommodate reusable medical devices and/or bracketry (e.g., dividers), as discussed above.

U-shaped cavity 718 further includes base 720 and sidewalls 722, 724, which define the height and width of cavity 718, respectively. However, as discussed above, cavity 718 is not limited to a specific height or width; rather, height/width dimensions may depend on the intended purpose of modular bracket assembly 700. Further, although depicted as two cavities 718, additional cavities may be included by merely increasing the size of bracket 702. The disclosed two cavity design is merely illustrative, and is not intended to be limiting. Indeed, implementations that include more or less than two cavities may be utilized.

Slot 708 further includes sidewalls 710, 712, which define the width of slot 708. Slot 708 extends from top surface 704 into U-shaped cavities 714, 716. In an exemplary embodiment, U-shaped cavities 714, 716 are substantially perpendicular and extend from centrally located slot 708. Slot 708 may provide access for insertion of reusable medical device and/or bracketry into U-shaped cavities 714, 716. However, given that U-shaped cavities 714, 716 extend from surface 726 through the opposing surface, surgical reusable medical devices and/or bracketry may further be inserted through one of those surfaces. Although depicted as two perpendicularly situated U-shaped cavities 714, 716, additional cavities may be included by merely increasing the size of bracket 702. Of note, the depicted orientation and design are merely illustrative and are not intended to be limiting. Indeed, designs with more or less than two cavities may be utilized.

In an exemplary embodiment, cavity sidewalls 722, 724 are substantially perpendicular to bottom surface 706. Such orientation provides firm boundaries for constraint of reusable medical devices and/or bracketry. However, as discussed above, cavity sidewalls 722, 724 may define a slight angle such that base 720 diameter is smaller than the width of the opening of cavity 718. By angling sidewalls 722, 724, as described above, larger-sized reusable medical devices and/or bracketry may be incorporated without altering the perimeter dimensions of bracket 702. The diameter of base 720 and the width of the opening of cavity 708 may be altered to satisfy the intended purpose of modular bracket assembly 700. Further, features (not shown) may assist in inserting reusable medical devices and/or bracketry into cavity 708. The design of such features (not shown) may include chamfered edges, radiused edges, as well as other geometries.

In another example, slot sidewalls 710, 712 are substantially perpendicular to bottom surface 706. As mentioned above, such orientation provides firm boundaries for constraint of reusable medical devices and/or bracketry. However, as further discussed above, slot sidewalls 710, 712 may define a slight angle such that the opening adjacent to U-shaped cavities 714, 716 is smaller in width than the opening of slot 708. By angling slot sidewalls 710, 712, as described above, larger-sized reusable medical devices and/or bracketry may be incorporated without altering the perimeter dimensions of bracket 702. The width of the opening adjacent to U-shaped cavities 714, 716 and the opening of cavity 708 may be altered to satisfy the intended purpose of modular bracket assembly 700. Further, features 728 may assist in inserting reusable medical devices and/or bracketry into slot 708. The design of such features 728 may include chamfered edges, radiused edges, as well as other geometries.

In another example, not shown, features may extend perpendicularly inward from face 726 so as to provide a location for insertion of a divider. The disclosed divider may provide an additional level of reusable medical device/instrument storage. The disclosed divider may perpendicularly intersect cavity 714, 716, 718 and slots 708 so as to create an additional level of storage. In such exemplary implementations, reusable medical devices may be inserted into a first level, e.g., the portion below the divider (not shown), and rested on a base of U-shaped cavities 714, 716, and also inserted into a second level, e.g., the portion above the divider (not shown), and rested on divider (not shown).

With reference to FIG. 15, a similar assembly to FIG. 14, modular bracket assembly 750 includes bracket 752 and clip 100. Clip 100 may be in direct or indirect contact with bracket 752. Attachment between clip 100 and bracket 752 may be accomplished by permanent or semi-permanent fastener 150, e.g., rivet, screw/bolt, nail, pin, adhesive, weld, etc. However, attachment between clip 100 and bracket 752 is not limited to fastener 150. For example, clip 100 and bracket 752 may be fabricated as one part or bracket 752 and/or clip 100 may include connecting features to interface the other, without additional fasteners. In an exemplary embodiment, clip 100 is attached to bracket 752 in an appropriately sized cutout located on end surface 753 of bracket 752. However, clip 100 may also be attached to surface 753 without a cutout. Clip 100 may further be attached to bottom surface 756. The above-mentioned clip 100 location(s) and attachment mechanism(s) is/are merely illustrative and are not intended to be limiting.

Bracket 752 includes top surface 754, bottom surface 756, and back surface 780, 782. Extending from top surface 754 towards bottom surface 756 is slot 758 which transitions into two substantially U-shaped cavities 764, 766. U-shaped cavities 764, 766 are situated perpendicular to each other. However, such orientation is merely illustrative of one potential layout and such layout is not intended to be limiting. Also included are two substantially U-shaped cavities 768. In an exemplary embodiment, in viewing bracket 752 from face 776, U-shaped cavities 768 are symmetrically located on either side of slot 758. U-shaped cavities 764, 766, 768 and slot 758 may accommodate reusable medical devices and/or bracketry (e.g., dividers), as discussed above.

Additionally, assembly 750 further includes back surface 780, 782 that encloses the area opposite face 776. Back surface 780 extends perpendicularly to sidewalls 772, 774 in close proximity to cavity 768. Similarly, back surface 782 extends perpendicularly to sidewalls 760, 762 in close proximity to cavities 758, 764, 766. Back surface 780, 782 creates a guard for one end of a reusable medical device/instrument, thereby ensuring the reusable medical device/instrument does not slide out the back of assembly 750. Further, hole 784 may be included to enable water drainage after sterilization. Hole 784 may also enable protrusion of the tip of an reusable medical device/instrument.

U-shaped cavity 768 further includes base 770 and sidewalls 772, 774, which define the height and width of cavity 768, respectively. However, as discussed above, cavity 768 is not limited to a specific height or width rather, height/width dimensions may be varied based on the intended purpose of modular bracket assembly 750. Further, although depicted as two cavities 768, additional cavities may be included by merely increasing the size of bracket 752. The disclosed two cavity design is merely illustrative and is not intended to be limiting. Indeed, implementations that include more or less than two cavities may be utilized.

Slot 758 further includes sidewalls 760, 762, which define the width of slot 758. Slot 758 extends from top surface 754 into U-shaped cavities 764, 766. In an exemplary embodiment, U-shaped cavities 764, 766 are substantially perpendicular and extend from centrally located slot 758. Slot 758 may provide access for insertion of reusable medical device/instrument and/or bracketry into U-shaped cavities 764, 766. However, given that U-shaped cavities 764, 766 extend from surface 776 towards back surface 780, 782 reusable medical devices and/or bracketry may further be inserted through surface 776. Although depicted as two perpendicularly situated U-shaped cavities 764, 766, additional cavities may be included by merely increasing the size of bracket 752. Of note, the orientation and design are not intended to be limiting, and designs that include more or less than two cavities may be utilized.

In an exemplary embodiment, cavity sidewalls 772, 774 are substantially perpendicular to bottom surface 756. Such orientation provides firm boundaries for constraint of reusable medical devices and/or bracketry. However, as discussed above, cavity sidewalls 772, 774 may define a slight angle such that base 770 diameter is smaller than the width of the opening of cavity 768. By angling sidewalls 772, 774, as described above, larger-sized reusable medical devices and/or bracketry may be incorporated without altering the perimeter dimensions of bracket 752. The diameter of base 770 and the width of the opening of cavity 758 may be altered to satisfy the intended purpose of modular bracket assembly 750. Further, features (not shown) may assist in inserting reusable medical devices and/or bracketry into cavity 758. The design of such features (not shown) may include chamfered edges, radiused edges, as well as other geometries.

In another example, slot sidewalls 760, 762 are substantially perpendicular to bottom surface 756. As mentioned above, such orientation provides firm boundaries for constraint of reusable medical devices and/or bracketry. However, as further discussed above, slot sidewalls 760, 762 may define a slight angle such that the opening adjacent to U-shaped cavities 764, 766 is smaller in width than the opening of slot 758. By angling slot sidewalls 760, 762, as described above, larger-sized reusable medical devices and/or bracketry may be incorporated without altering the perimeter dimensions of bracket 752. The width of the opening adjacent to U-shaped cavities 764, 766 and the opening of cavity 758 may be altered to satisfy the intended purpose of modular bracket assembly 750. Further, features 778 may assist in inserting reusable medical devices and/or bracketry into slot 758. The design of such features 778 may include chamfered edges, radiused edges, as well as other geometries.

In another example, not shown, features may extend perpendicularly inward from face 776 so as to provide a location for insertion of a divider. The disclosed divider may provide an additional level of reusable medical device/instrument storage. The disclosed divider may perpendicularly intersect cavity 764, 766, 768 and slots 758 so as to create an additional level of storage. In such exemplary implementations, reusable medical devices may be inserted into a first level, e.g., the portion below the divider (not shown), and rested on a base of U-shaped cavities 764, 766, and also inserted into a second level, e.g., the portion above the divider (not shown), and rested on divider (not shown).

With regards to FIGS. 16A and 16B, assembly 800 includes bracket assemblies 850, 900, 950, 1000, 1050, 1100, 1150, 1200, 1250, 1300, 1350, 1400, 1450, 1500, however, the disclosed brackets are not limited to assembly 800 and may further be integrated into assembly 10. Additionally, brackets 200, 250, 300, 350, 400, 450, 500, 550, 600, 650, 700, 750 may be integrated into assembly 800. Accordingly, the disclosed bracket assemblies are interchangeable between the two assemblies. Assembly 10, 800 are merely illustrative of potential layouts based on a given surgical procedure. The layout of assembly 10, 800 is not intended to be limiting.

With reference to FIGS. 16A-16C, assembly 800 advantageously depicts a potential layout of various modular brackets 850, 900, 950, 1000, 1050, 1100, 1150, 1200, 1250, 1300, 1350, 1400, 1450 mounted in relation to tray 12. As discussed above, tray 12 includes perforations 30 which allow sanitization of tray components (e.g., reusable medical devices, instruments, bracket assemblies, etc.) and enable modular bracket connection.

With specific reference to assembly 800, not depicted in assembly 10, but included, is clasp mechanism 34 for retention of cover 13. Cover 13 may further include a non-perforated portion 15 for display of reference information, e.g., surgery number, patient name, reusable medical devices included within tray 12, hospital name, doctor name, and the like.

With reference to FIG. 17, modular bracket assembly 850 includes bracket 852 and clip 100. Clip 100 may be in direct or indirect contact with bracket 852. Attachment between clip 100 and bracket 852 may be accomplished by permanent or semi-permanent fastener 150, e.g., rivet, screw/bolt, nail, pin, adhesive, weld, etc. However, attachment between clip 100 and bracket 852 is not limited to fastener 150. For example, clip 100 and bracket 852 may be fabricated as one part or bracket 852 and/or clip 100 may include connecting features to interface the other, without additional fasteners. In an exemplary embodiment, clip 100 is attached to bracket 852 in an appropriately sized cutout located on end surface 853 of bracket 852. However, clip 100 may also be attached to surface 853 without a cutout. Clip 100 may further be attached to bottom surface 856. The above-mentioned clip 100 location(s) and attachment mechanism(s) is/are merely illustrative and are not intended to be limiting.

Bracket 852 includes top surface 854 and bottom surface 856. Extending from top surface 854 towards bottom surface 856 is slot 858, 866. Slot 858, 866 may accommodate reusable medical devices and/or bracketry (e.g., dividers), as discussed above. In an exemplary embodiment, slot 858 includes base 860 and sidewalls 862, 864, which define the height and width of slot 858, respectively. Sidewalls 862, 864 are substantially perpendicular to base 860. Such orientation provides firm boundaries for constraint of reusable medical devices and/or bracketry. However, sidewalls 862, 864 may be angled such that the width of base 860 is smaller than the opening of slot 858, which is located on top surface 854. By angling sidewalls 862, 864, larger-sized reusable medical devices and/or bracketry may be incorporated without altering the perimeter dimensions of bracket 852. The width of base 860 and the opening of cavity 858 may be altered to satisfy the intended purpose of modular bracket assembly 850.

Slot 866 includes base 868 and sidewalls 872, 874, which define the height and width of slot 866, respectively. Base 868 further includes feature 870 for retention of a feature included on a reusable medical device. Feature 870 may provide alignment capabilities to ensure the reusable medical device is oriented and maintained in a particular position (e.g., open position) for the duration until aseptic presentation. Sidewalls 872, 874 are substantially perpendicular to base 868. As mentioned above, such orientation provides firm boundaries for constraint of reusable medical devices and/or bracketry. However, as further discussed above, sidewalls 872, 874 may be angled such that the width of base 868 is smaller than the opening of slot 866, which is located on top surface 854. By angling sidewalls 872, 874, as described above, larger-sized reusable medical devices and/or bracketry may be incorporated without altering the perimeter dimensions of bracket 852. The width of base 868 and the opening of cavity 866 may be altered to satisfy the intended purpose of modular bracket assembly 850.

Slots 858, 866 may further include features 878 to assist in inserting reusable medical devices and/or bracketry therein. The design of such features 878 may include chamfered edges, radiused edges, as well as other geometries. Although modular bracket assembly 850 is depicted with two slots 858, 866, additional slots may be included by merely increasing the size of bracket 852. The disclosed two slot design is merely illustrative and is not intended to be limiting; indeed, more or less than two slots may be incorporated.

In another example, not shown, features may extend perpendicularly inward from face 876 so as to provide a location for insertion of a divider. The disclosed divider may provide an additional level of reusable medical device/instrument storage. The disclosed divider may perpendicularly intersect slots 858, 866 so as to create said additional level of storage. In such exemplary embodiments, reusable medical devices may be inserted into a first level, e.g., the portion below the divider (not shown), and rested on base 860, 868 and also inserted into a second level, e.g., the portion above the divider (not shown), and rested on divider (not shown).

With reference to FIG. 18, modular bracket assembly 900 includes bracket 902 and clip 100. Clip 100 may be in direct or indirect contact with bracket 902. Attachment between clip 100 and bracket 902 may be accomplished by permanent or semi-permanent fastener 150, e.g., rivet, screw/bolt, nail, pin, adhesive, weld, etc. However, attachment between clip 100 and bracket 902 is not limited to fastener 150. For example, clip 100 and bracket 902 may be fabricated as one part or bracket 902 and/or clip 100 may include connecting features to interface the other, without additional fasteners. In an exemplary embodiment, clip 100 is attached to bracket 902 in an appropriately sized cutout located on end surface 903 of bracket 902. However, clip 100 may also be attached to surface 903 without a cutout. Clip 100 may further be attached to bottom surface 906. The above-mentioned clip 100 location(s) and attachment mechanism(s) is/are merely illustrative and are not intended to be limiting.

Bracket 902 includes top surface 904 and bottom surface 906. Extending from top surface 904 towards bottom surface 906 is slot 908, 916. Slot 908, 916 may accommodate reusable medical devices and/or bracketry (e.g., dividers), as discussed above. In an exemplary embodiment, slot 908 includes base 910 and sidewalls 912, 914, which define the height and width of slot 908, respectively. Sidewalls 912, 914 are substantially perpendicular to base 910. Such orientation provides firm boundaries for constraint of reusable medical devices and/or bracketry. However, sidewalls 912, 914 may be angled such that the width of base 910 is smaller than the opening of slot 908, which is located on top surface 904. By angling sidewalls 912, 914, larger-sized reusable medical devices and/or bracketry may be incorporated without altering the perimeter dimensions of bracket 902. The width of base 910 and the opening of cavity 908 may be altered to satisfy the intended purpose of modular bracket assembly 900.

Slot 916 includes base 918 and sidewalls 920, 922, which define the height and width of slot 916, respectively. Sidewalls 920, 922 are substantially perpendicular to bottom base 918. As mentioned above, such orientation provides firm boundaries for constraint of reusable medical devices and/or bracketry. However, as further discussed above, sidewalls 920, 922 may be angled such that the width of base 918 is smaller than the opening of slot 916, which is located on top surface 904. By angling sidewalls 920, 922, as described above, larger-sized reusable medical devices and/or bracketry may be incorporated without altering the perimeter dimensions of bracket 902. The width of base 918 and the opening of cavity 916 may be altered to satisfy the intended purpose of modular bracket assembly 900.

Slots 908, 916 may further include features 926 to assist in inserting reusable medical devices and/or bracketry therein. The design of such features 926 may include chamfered edges, radiused edges, as well as other geometries. Although modular bracket assembly 900 is depicted with two slots 908, 916, additional slots may be included by merely increasing the size of bracket 902. The disclosed two slot design is merely illustrative and is not intended to be limiting; indeed, more or less than two slots may be utilized.

In another example, not shown, features may extend perpendicularly inward from face 924 so as to provide a location for insertion of a divider. The disclosed divider may provide an additional level of reusable medical device/instrument storage. The disclosed divider may perpendicularly intersect slots 908, 916 so as to create an additional level of storage. In such exemplary implementations, reusable medical devices may be inserted into a first level, e.g., the portion below the divider (not shown), and rested on base 910, 918 and also inserted into a second level, e.g., the portion above the divider (not shown), and rested on divider (not shown).

With reference to FIGS. 19 and 20, modular bracket assembly 950, 1000 includes bracket 952, 1002 and clip 100. Comparison of the two bracket assemblies assists in illustrating variously-sized slots. Clip 100 may be in direct or indirect contact with bracket 952, 1002. Attachment between clip 100 and bracket 952, 1002 may be accomplished by permanent or semi-permanent fastener 150, e.g., rivet, screw/bolt, nail, pin, adhesive, weld, etc. However, attachment between clip 100 and bracket 952, 1002 is not limited to fastener 150. For example, clip 100 and bracket 952, 1002 may be fabricated as one part or bracket 952, 1002 and/or clip 100 may include connecting features to interface the other, without additional fasteners. In an exemplary embodiment, clip 100 is attached to bracket 952, 1002 in an appropriately sized cutout located on end surface 953, 1003 of bracket 952, 1002. However, clip 100 may also be attached to surface 953, 1003 without a cutout. Clip 100 may further be attached to bottom surface 956, 1006. The above-mentioned clip 100 location(s) and attachment mechanism(s) is/are merely illustrative and are not intended to be limiting.

Bracket 952, 1002 includes top surface 954, 1004 and bottom surface 956, 1006. Extending from top surface 954, 1004 towards bottom surface 956, 1006 is slot 958, 966, 1008, 1016. Slot 958, 966, 1008, 1016 may accommodate reusable medical devices and/or bracketry (e.g., dividers), as discussed above. In an exemplary embodiment, slot 958, 1008 includes base 960, 1010 and sidewalls 962, 964, 1012, 1014, which define the height and width of slot 958, 1008 respectively. Sidewalls 962, 964, 1012, 1014 are substantially perpendicular to base 960, 1010. Such orientation provides firm boundaries for constraint of reusable medical devices and/or bracketry. However, sidewalls 962, 964, 1012, 1014 may be angled such that the width of base 960, 1010 is smaller than the opening of slot 958, 1008, which is located on top surface 954, 1004. By angling sidewalls 962, 964, 1012, 1014, larger-sized reusable medical devices and/or bracketry may be incorporated without altering the perimeter dimensions of bracket 952, 1002. The width of base 960, 1010 and the opening of cavity 958, 1008 may be altered to satisfy the intended purpose of modular bracket assembly 950, 1000.

Slot 966, 1016 includes base 968, 1018 and sidewalls 970, 972, 1020, 1022, which define the height and width of slot 966, 1016, respectively. Sidewalls 970, 972, 1020, 1022 are substantially perpendicular to bottom base 968, 1018. As mentioned above, such orientation provides firm boundaries for constraint of reusable medical devices and/or bracketry. However, as further discussed above, sidewalls 970, 972, 1020, 1022 may be angled such that the width of base 968, 1018 is smaller than the opening of slot 966, 1016, which is located on top surface 954, 1004. By angling sidewalls 970, 972, 1020, 1022, as described above, larger-sized reusable medical devices and/or bracketry may be incorporated without altering the perimeter dimensions of bracket 952, 1002. The width of base 968, 1018 and the opening of cavity 966, 1016 may be altered to satisfy the intended purpose of modular bracket assembly 950, 1000.

Slots 958, 966, 1008, 1016 may further include features 976, 1026 to assist in inserting reusable medical devices and/or bracketry therein. The design of such features 976, 1026 may include chamfered edges, radiused edges, as well as other geometries. Although modular bracket assembly 950, 1000 is depicted with two slots 958, 966, 1008, 1016, additional slots may be included by merely increasing the size of bracket 952, 1002. The disclosed two slot design is merely illustrative and is not intended to be limiting; rather, more or less than two slots may be utilized.

In another example, not shown, features may extend perpendicularly inward from face 974, 1024 so as to provide a location for insertion of a divider. The disclosed divider may provide an additional level of reusable medical device/ instrument storage. The disclosed divider may perpendicularly intersect slots 958, 966, 1008, 1016 so as to create an additional level of storage. In such exemplary embodiments, reusable medical devices may be inserted into a first level, e.g., the portion below the divider (not shown), and rested on base 960, 968, 1010, 1018 and also inserted into a second level, e.g., the portion above the divider (not shown), and rested on divider (not shown).

With reference to FIG. 21, modular bracket assembly 1050 includes bracket 1052 and clip 100. Clip 100 may be in direct or indirect contact with bracket 1052. Attachment between clip 100 and bracket 1052 may be accomplished by permanent or semi-permanent fastener 150, e.g., rivet, screw/bolt, nail, pin, adhesive, weld, etc. However, attachment between clip 100 and bracket 1052 is not limited to fastener 150. For example, clip 100 and bracket 1052 may be fabricated as one part or bracket 1052 and/or clip 100 may include connecting features to interface the other, without additional fasteners. In an exemplary embodiment, clip 100 is attached to bracket 1052 in an appropriately sized cutout located on end surface 1053 of bracket 1052. However, clip 100 may also be attached to surface 1053 without a cutout. Clip 100 may further be attached to bottom surface 1056. The above-mentioned clip 100 location(s) and attachment mechanism(s) is/are merely illustrative and are not intended to be limiting.

Bracket 1052 includes top surface 1054 and bottom surface 1056. Extending from top surface 1054 towards bottom surface 1056 is slot 1058. Slot 1058 may accommodate reusable medical devices and/or bracketry (e.g., dividers). In an exemplary embodiment, slot 1058 includes base 1060 and sidewalls 1062, 1064, which define the height and width of slot 1058, respectively. Although modular bracket assembly 1050 is depicted with five identical slots 1058, slot 1058 design and quantity may be adjusted without departing from the spirit/scope of the disclosure. For instance, modular bracket 1052 may include five variously-sized slots 1058.

Sidewalls 1062, 1064 are substantially perpendicular to base 1060. Such orientation provides firm boundaries for constraint of reusable medical devices and/or bracketry. However, sidewalls 1062, 1064 may be angled such that the width of base 1060 is smaller than the opening of slot 1058, which is located on top surface 1054. By angling sidewalls 1062, 1064, larger-sized reusable medical devices and/or bracketry may be incorporated without altering the perimeter dimensions of bracket 1052. The width of base 1060 and the opening of slot 1058 may be altered to satisfy the intended purpose of modular bracket assembly 1050. Slot 1058 may further include features 1068 to assist in inserting reusable medical devices and/or bracketry therein. The design of such features 1068 may include chamfered edges, radiused edges, as well as other geometries.

In another example, not shown, features may extend perpendicularly inward from face 1066 so as to provide a location for insertion of a divider. The disclosed divider may provide an additional level of reusable medical device/instrument storage. The disclosed divider may perpendicularly intersect slot 1058 so as to create an additional level of storage. In such exemplary implementations, reusable medical devices may be inserted into a first level, e.g., the portion below the divider (not shown), and rested on base 1060 and also inserted into a second level, e.g., the portion above the divider (not shown), and rested on divider (not shown).

With reference to FIG. 22, modular bracket assembly 1100 includes bracket 1102 and clip 100. Clip 100 may be in direct or indirect contact with bracket 1102. Attachment between clip 100 and bracket 1102 may be accomplished by permanent or semi-permanent fastener 150, e.g., rivet, screw/bolt, nail, pin, adhesive, weld, etc. However, attachment between clip 100 and bracket 1102 is not limited to fastener 150. For example, clip 100 and bracket 1102 may be fabricated as one part or bracket 1102 and/or clip 100 may include connecting features to interface the other, without additional fasteners. In an exemplary embodiment, clip 100 is attached to bracket 1102 in an appropriately sized cutout located on end surface 1103 of bracket 1102. However, clip 100 may also be attached to surface 1103 without a cutout. Clip 100 may further be attached to bottom surface 1106. The above-mentioned clip 100 location(s) and attachment mechanism(s) is/are merely illustrative and are not intended to be limiting.

Bracket 1102 includes top surface 1104 and bottom surface 1106. Extending from top surface 1104 towards bottom surface 1106 is slot 1108. Slot 1108 may accommodate reusable medical devices and/or bracketry (e.g., dividers). In an exemplary embodiment, slot 1108 includes base 1110 and sidewalls 1112, 1114, which define the height and width of slot 1108, respectively. Although modular bracket assembly 1100 is depicted with four identical slots 1108, slot 1108 design and quantity may be adjusted without departing from the spirit/scope of the disclosure. For instance, modular bracket 1102 may include four variously-sized slots 1108.

Sidewalls 1112, 1114 are substantially perpendicular to base 1110. Such orientation provides firm boundaries for constraint of reusable medical devices and/or bracketry. However, sidewalls 1112, 1114 may be angled such that the width of base 1110 is smaller than the opening of slot 1108, which is located on top surface 1104. By angling sidewalls 1112, 1114, larger-sized reusable medical devices and/or bracketry may be incorporated without altering the perimeter dimensions of bracket 1102. The width of base 1110 and the opening of slot 1108 may be altered to satisfy the intended purpose of modular bracket assembly 1100. Slot 1108 may further include features 1118 to assist in inserting reusable medical devices and/or bracketry therein. The design of such features 1118 may include chamfered edges, radiused edges, as well as other geometries.

In another example, not shown, features may extend perpendicularly inward from face 1116 so as to provide a location for insertion of a divider. The disclosed divider may provide an additional level of reusable medical device/instrument storage. The disclosed divider may perpendicularly intersect slot 1108 so as to create an additional level of storage. In such exemplary embodiments, reusable medical devices may be inserted into a first level, e.g., the portion below the divider (not shown), and rested on base 1110 and also inserted into a second level, e.g., the portion above the divider (not shown), and rested on divider (not shown).

With reference to FIG. 23, modular bracket assembly 1150 includes bracket 1152 and clip 100. Clip 100 may be in direct or indirect contact with bracket 1152. Attachment between clip 100 and bracket 1152 may be accomplished by permanent or semi-permanent fastener 150, e.g., rivet, screw/bolt, nail, pin, adhesive, weld, etc. However, attachment between clip 100 and bracket 1152 is not limited to fastener 150. For example, clip 100 and bracket 1152 may be fabricated as one part or bracket 1152 and/or clip 100 may include connecting features to interface the other, without additional fasteners. In an exemplary embodiment, clip 100 is attached to bracket 1152 in an appropriately sized cutout located on end surface 1153 of bracket 1152. However, clip 100 may also be attached to surface 1153 without a cutout. Clip 100 may further be attached to bottom surface 1156.

The above-mentioned clip 100 location(s) and attachment mechanism(s) is/are merely illustrative and are not intended to be limiting.

Bracket 1152 includes top surface 1154 and bottom surface 1156. Extending from top surface 1154 towards bottom surface 1156 is slot 1158, 1164. Slot 1158, 1164 may accommodate reusable medical devices and/or bracketry (e.g., dividers). In an exemplary embodiment, slots 1158, 1164 oppose each other and are separated by base 1170, which extends a substantial portion of the cross-section of bracket 1152, located between top surface 1154 and bottom surface 1156. Base 1170 is defined by cavity 1174, which resembles a tunnel, separating slots 1158, 1164. The following disclosure will discuss each slot 1158, 1164 separately; however, unless otherwise stated, each slot 1158, 1164 includes the same features, but with different reference numbers.

Slot 1158 includes base 1170, as discussed above, and sidewalls 1160, 1162, which define the height and width of slot 1158, respectively. Bracket 1152 further includes four equally-sized slots 1158 adjacent to each other. However, slot 1158 design and quantity may be adjusted without departing from the spirit/scope of the disclosure. For instance, modular bracket 1152 may include four variously-sized slots 1158.

Opposing slot 1158 is slot 1164, which, as mentioned above, shares base 1170. Although depicted as opposing, slot 1158 and slot 1164 may be off centered such that slot 1158 opposes wall 1174 and slot 1164 opposes wall 1176. Walls 1174, 1176 define cavity 1174. Slot 1164 includes base 1170, as discussed above, and sidewalls 1166, 1168, which define the height and width of slot 1164, respectively. Bracket 1152 further includes four equally-sized slots 1164 adjacent to each other. However, slot 1164 design and quantity may be adjusted without departing from the spirit/ scope of the disclosure. For instance, modular bracket 1152 may include four variously-sized slots 1164.

Sidewalls 1160, 1162, 1166, 1168 are substantially perpendicular to base 1170. Such orientation provides firm boundaries for constraint of reusable medical devices and/or bracketry. However, sidewalls 1160, 1162, 1166, 1168 may be angled such that the width of base 1170 is smaller than the opening of slot 1158, 1164, which is located on top surface 1154. By angling sidewalls 1112, 1114, 1166, 1168, larger-sized reusable medical devices and/or bracketry may be incorporated without altering the perimeter dimensions of bracket 1152. The width of base 1170 and the opening of slot 1158, 1164 may be altered to satisfy the intended purpose of modular bracket assembly 1150. Slot 1158, 1164 may further include features (not shown) to assist in inserting reusable medical devices and/or bracketry therein. The design of such features (not shown) may include chamfered edges, radiused edges, as well as other geometries.

In operation, reusable medical devices and/or bracketry may be inserted in close relation to slot 1158, 1164. In an exemplary embodiment, slots 1158, 1164 may each include different reusable medical device/instrument/bracketry inserted in close proximity thereto. For example, slot 1158 may include a reusable medical device and slot 1164, either opposing or non-opposing slot 1158, may include a bracketry. Of note, the selection of reusable medical device/ instrument and/or bracketry is merely illustrative. However, in another example, slot 1158 and slot 1164 include the same reusable medical device that extends across base 1170. In another embodiment, slot 1158, 1164 and cavity 1174 each include separate reusable medical devices/bracketry.

In another example, not shown, features may extend perpendicularly inward from face 1178 so as to provide a location for insertion of a divider. The disclosed divider may provide an additional level of reusable medical device/ instrument storage. The disclosed divider may perpendicularly intersect slot 1158, 1164 so as to create an additional level of storage. In such exemplary embodiment, reusable medical devices may be inserted into a first level, e.g., the portion below the divider (not shown), and rested on base 1170 and also inserted into a second level, e.g., the portion above the divider (not shown), and rested on divider (not shown).

With reference to FIG. 24, modular bracket assembly 1200 includes bracket 1202 and clip 100. Clip 100 may be in direct or indirect contact with bracket 1202. Attachment between clip 100 and bracket 1202 may be accomplished by permanent or semi-permanent fastener 150, e.g., rivet, screw/bolt, nail, pin, adhesive, weld, etc. However, attachment between clip 100 and bracket 1202 is not limited to fastener 150. For example, clip 100 and bracket 1202 may be fabricated as one part or bracket 1202 and/or clip 100 may include connecting features to interface the other, without additional fasteners. In an exemplary embodiment, clip 100 is attached to bracket 1202 in an appropriately sized cutout located on end surface 1203 of bracket 1202. However, clip 100 may also be attached to surface 1203 without a cutout. Clip 100 may further be attached to bottom surface 1206. The above-mentioned clip 100 location(s) and attachment mechanism(s) is/are merely illustrative and are not intended to be limiting.

Bracket 1202 includes top surface 1204, bottom surface 1206, and ledge 1208. Extending from top surface 1204 to ledge 1208 is cavity 1210. Cavity 1210 includes back surface 1212 and sidewall 1214. Back surface 1212 and sidewall 1214 may be further connected by radiused corner 1216. In an exemplary embodiment, cavity 1210 captures caddy 1350, 1400, as will be discussed in connection with FIGS. 27 and 28 in view of FIG. 16. Cavity 1210 may further contain larger reusable medical devices/bracketry that is/are in close proximity to ledge 1208.

Extending from ledge 1208 towards bottom surface 1206 is slot 1218. Slot 1218 may accommodate reusable medical devices and/or bracketry (e.g., dividers). In an exemplary embodiment, slot 1218 includes sidewalls 1220, 1222, which define the width of slot 1218. Although modular bracket assembly 1200 is depicted with five identical slots 1218, slot design and quantity may be adjusted without departing from the spirit/scope of the disclosure. For instance, modular bracket 1202 may include five variously-sized slots 1218. Although depicted with as a bottomless slot 1218, a bottom to the slot may be included to additionally retain surgical reusable medical devices and/or bracketry.

In another example, not shown, features may extend perpendicularly inward from face 1224 so as to provide a location for insertion of a divider. The disclosed divider may provide an additional level of reusable medical device/ instrument storage. The disclosed divider may perpendicularly intersect slot 1218 so as to create an additional level of storage. In such exemplary embodiments, reusable medical devices may be inserted into a first level, e.g., the portion below the divider (not shown), and rested on base (not shown) and also inserted into a second level, e.g., the portion above the divider (not shown), and rested on divider (not shown).

With reference to FIG. 25, modular bracket assembly 1250 includes bracket 1252 and clip 100. Clip 100 may be in direct or indirect contact with bracket 1252. Attachment between clip 100 and bracket 1252 may be accomplished by permanent or semi-permanent fastener 150, e.g., rivet, screw/bolt, nail, pin, adhesive, weld, etc. However, attachment between clip 100 and bracket 1252 is not limited to fastener 150. For example, clip 100 and bracket 1252 may be fabricated as one part or bracket 1252 and/or clip 100 may include connecting features to interface the other, without additional fasteners. In an exemplary embodiment, clip 100 is attached to bracket 1252 in an appropriately sized cutout located on end surface 1253 of bracket 1252. However, clip 100 may also be attached to surface 1253 without a cutout. Clip 100 may further be attached to bottom surface 1256. The above-mentioned clip 100 location(s) and attachment mechanism(s) is/are merely illustrative and are not intended to be limiting.

Bracket 1252 includes top surface 1254 and bottom surface 1256. In an exemplary embodiment, looking at the profile of bracket 1252, at least two variously-sized rectangles are stacked on top of each other. However, one-sized rectangle may be used, without departing from the scope/spirit of this disclosure. Specifically, with one larger rectangle as the base and a smaller as the top, material may be saved as compared to a one-sized rectangle. The disclosed top rectangle includes top surface 1254 and side surface 1258. The bottom surface of top rectangle is the top surface of a base rectangle (not shown). The base rectangle includes bottom surface 1256 and side surface 1260. A diagonal feature 1262 transitions between top rectangle and bottom rectangle.

Modular bracket assembly 1250 may be used to raise reusable medical devices and/or bracketry off tray 12 or to support caddy 1350, 1400, as will be discussed with reference to FIGS. 27 and 28 in view of FIG. 16.

With reference to FIG. 26, bracketry (e.g., divider) 1300 includes top surface 1302, bottom surface 1304, side surface 1306, front surface 1308, and back surface 1316. Bracketry 1300 may be substantially rectangular where top surface 1302 and bottom surface 1304 are longer than side surface 1306. However, the dimensions and design are merely illustrative and are not intended to be limiting.

As depicted in FIG. 16B, bracketry 1300 may be used as a divider, e.g., extending between bracket assembly 1250. In an exemplary embodiment, at least two bracketry 1300 may be assembled parallel to each other to define a box (see FIG. 16B). Bracketry 1300 further includes a plurality of perforations 1310 that extend between front surface 1308 and back surface 1316. Perforations 1310 may be used to facilitate central sterile processing processes of components stored within the disclosed bracketry 1300 box. Slots 1312 may further facilitate central sterile processing processes of components housed within the disclosed bracketry 1300 box. Slots 1312 may also be used as retention features to secure bracketry 1300 to a bracket assembly. Further, blank space 1314 may be used to display identifying information to distinguish each bracketry 1300 box. The disclosed information may include surgery number, patient name, reusable medical devices included, hospital name, doctor name, among others, as will be apparent to persons skilled in the art.

With reference to FIG. 27A, caddy assembly 1350 includes caddy 1352 and cover 1450. FIG. 27B depicts caddy 1352, which may be substantially rectangular; however, additional or alternative geometric designs may be used. Caddy 1352 includes parallel top surface 1354 and bottom surface 1356, which are connected by first sidewall 1358, second sidewall 1360, and third sidewall 1361. First sidewall 1358 is attached directly/indirectly in relation to second sidewall 1360 and third sidewall 1361 to form the perimeter of a box. First sidewall 1358, second sidewall 1360, and third sidewall 1361 may be connected by radiused edge 1362; however, additional corner edge features may be used, for example, a bevel, a 90 degree corner, among others. Second sidewall 1360 may have bottom surface 1364 that is shallower than bottom surface 1356 of caddy 1352. Such shallower bottom surface 1364 enables caddy 1352 to slide along divider 1300 with first sidewall 1358 located on the exterior of divider 1300.

In an exemplary embodiment, top surface 1354 and cavity surface 1366 combine to form at least a majority of outermost surface of caddy 1352. Top surface 1354 and cavity surface 1366 may be substantially parallel, with cavity surface 1366 located some distance beneath top surface 1354, i.e., located further within caddy 1352. Top surface 1354 may be located on first sidewall 1358 and second sidewall 1360. Third sidewall 1361 may not include top surface 1354 to allow cover 1450 to slid along cavity surface 1366, unobstructed. Inside edge of top surface 1354 and cavity surface 1366 are separated by step 1368. Step 1368 may be the same height as the thickness of cover 1450. In one example, step 1368 is located only along first sidewall 1358. In such case, the portion along second sidewall 1360 may be left open such that cover 1450 may slide beneath top surface 1354. In another example, cover 1450 may slide beneath top surface 1354, within a channel (not shown), along first sidewall 1358 and second sidewall 1360. In yet another example, step 1368 is located on first sidewall 1358 and second sidewall 1360.

Located on cavity surface 1366 are cavities 1370, which may be used to store small, delicate components, e.g., reusable medical devices, implants, etc., that require central sterile processing processes. Although depicted as identical cavities 1370, additional designs may be used, as further depicted in FIG. 28B.

With reference to FIG. 28A, caddy assembly 1400 includes caddy 1402 and cover 1400. FIG. 28B depicts caddy 1402, which may be substantially rectangular; however, additional or alternative designs may be used. Caddy 1402 includes parallel top surface 1404 and bottom surface 1406, which are connected together by first sidewall 1408, second sidewall 1410, and third sidewall 1411. First sidewall 1408 is attached directly/indirectly in relation to second sidewall 1410 and third sidewall 1411 to form the perimeter of a box. First sidewall 1408, second sidewall 1410, and third sidewall 1411 may be connected by radiused edge 1412; however, additional corner edge features may be used, for example, a bevel, a 90 degree corner, among others. Second sidewall 1410 may have bottom surface 1414 that is shallower than bottom surface 1406 of caddy 1402. Such shallower bottom surface 1414 enables caddy 1402 to slide along divider 1300 with first sidewall 1408 engaged with divider 1300.

In an exemplary embodiment, top surface 1404 and cavity surface 1416 combine to form at least a majority of outermost surface of caddy 1402. Top surface 1404 and cavity surface 1416 may be substantially parallel, with cavity surface 1416 located some distance beneath top surface, i.e., located further within caddy 1402. Top surface 1414 may be located on first sidewall 1408 and second sidewall 1410. Third sidewall 1411 may not include top surface to allow cover 1450 to slid along cavity surface 1416, unobstructed. Inside edge of top surface 1404 and cavity surface 1416 are separated by step 1418. Step 1418 may be the same height as the thickness of cover 1450. In one example, step 1418 is located only along first sidewall 1408. In such case, the portion along second sidewall 1410 may be left open such that cover 1450 may slide beneath top surface 1404. In another example, cover 1450 may slide beneath top surface 1404, within a channel (not shown), along first sidewall 1408 and second sidewall 1410. In yet another example, step 1418 is located on first sidewall 1408 and second sidewall 1410.

Located on cavity surface 1416 are cavities 1420, 1422, which may be used to store small, delicate components, e.g., reusable medical devices, implants, etc., that require central sterile processing processes. Cavities 1420, 1422 may include various features to properly capture the disclosed small, delicate components.

With reference to FIG. 29, cover 1450 includes first sidewall 1452, second sidewall 1454, and surface 1456. Cover 1450 may be substantially rectangular where first sidewall 1452 is longer than second sidewall 1454. However, the dimensions and design are merely illustrative and are not intended to be limiting. In an exemplary embodiment, cover 1450 is dimensioned similarly as to the dimensions of caddy 1352, 1402.

As depicted in FIGS. 27A and 28A, cover 1450 interfaces with caddy 1352, 1402, specifically with top surface 1354, 1404 and cavity surface 1366, 1416. Cover 1450 further includes a plurality of perforations 1458 that extend between front surface 1308 and back surface 1316. Perforations 1458 may be used to facilitate central sterile processing processes of those components housed within caddy 1352, 1402. Slots 1460 may further facilitate central sterile processing processes of those components housed within caddy 1352, 1402. Slots 1460 may also be used as retention features to secure cover 1450 to caddy 1352, 1402. Feature 1462 may be used as another retention feature to secure cover 1450 to caddy 1352, 1402. Such retention may occur beneath top surface 1354, 1404 of caddy 1352, 1402, but above cavity surface 1366, 1416. Hole 1464 may further be used as a retention feature, as mentioned above. Further, blank space 1466 may be used to display identifying information to distinguish each caddy assembly 1350, 1400. The disclosed information may include surgery number, patient name, reusable medical devices included, hospital name, doctor name, among others, as will be apparent to persons skilled in the art.

In operation, as depicted in FIGS. 16A and 16B, caddy assembly 1350, 1400 may be in direct or indirect contact with bracket assembly 1200. In an exemplary embodiment, base 1356, 1406 of caddy assembly 1350, 1400 may be in contact with ledge 1208 of bracket assembly 1200. Additionally, second sidewall 1360, 1410 and radiused edge 1362, 1412 may interface with cavity 1210 of bracket assembly 1200. Specifically, the perimeter of caddy 1352, 1402 is substantially similar to the dimensions of cavity 1210. By raising caddy assembly 1350, 1400 off tray 12, additional storage space may be used beneath caddy assembly 1350, 1400, as depicted in FIG. 16B, where caddy assembly 1350, 1400 is hidden.

In an exemplary embodiment, beneath caddy assembly 1350, 1400, bracketry 1300 may be used to create an additional box beneath caddy assembly 1350. To ensure sufficient contact between caddy assembly 1350 and bracketry 1300, raised base 1364 of second sidewall 1360 allows bracketry 1300 to fit beneath caddy assembly 1350 and allow first sidewall 1358 to overlap bracketry 1300. Although depicted as caddy assembly 1350, caddy assembly 1400 or other designs (not depicted), may replace caddy assembly 1350 and additional bracketry may be used without departing from the spirit/scope of this disclosure.

In another exemplary embodiment, beneath caddy assembly 1400, bracket assembly 1050 may be positioned so as to allow a second level of storage. Although depicted as caddy assembly 1400, caddy assembly 1350 or other designs (not depicted), may replace caddy assembly 1400 and additional bracket assembly may be used without departing from the spirit/scope of this disclosure. The disclosed under-caddy storage overcomes a shortcoming of current tray assemblies, maximizing tray usage.

With reference to FIGS. 30A-30C, swivel bracket assembly 1500 includes first bracket 1502, second bracket 1550 and clip 100. Clip 100 may be in direct or indirect contact with first bracket 1502. Attachment between clip 100 and first bracket 1502 may be accomplished by permanent or semi-permanent fastener 150, e.g., rivet, screw/bolt, nail, pin, adhesive, weld, etc. However, attachment between clip 100 and first bracket 1502 is not limited to fastener 150. For example, clip 100 and first bracket 1502 may be fabricated as one part or first bracket 1502 and/or clip 100 may include connecting features to interface the other, without additional fasteners. In an exemplary embodiment, clip 100 is attached to first bracket 1502 in an appropriately sized cutout located on end surface 1503 of first bracket 1502. However, clip 100 may also be attached to surface 1503 without a cutout. Clip 100 may further be attached to bottom surface 1506 of first bracket 1502. The above-mentioned clip 100 location(s) and attachment mechanism(s) is/are merely illustrative and are not intended to be limiting.

First bracket 1502 includes top surface 1504 and bottom surface 1506. Extending from top surface 1504 to bottom surface 1506 is slot 1508. Slot 1508 may accommodate reusable medical devices and/or bracketry (e.g., dividers). In an exemplary embodiment, slot 1508 includes base 1510 and sidewalls 1512, 1514, which define the height and width of slot 1508, respectively. Although modular bracket assembly 1500 is depicted with four identical slots 1508, slot 1508 design and quantity may be adjusted without departing from the spirit/scope of the disclosure. For instance, first bracket 1502 may include four variously-sized slots 1508. First bracket 1502 further includes raised feature 1518 with surface 1520 for interaction with second bracket 1550, as discussed below.

Second bracket 1550 includes top surface 1552 and bottom surface 1554. Extending from top surface 1552 to bottom surface 1554 is slot 1556. Slot 1556 may accommodate reusable medical devices and/or bracketry (e.g., dividers). In an exemplary embodiment, slot 1556 includes base 1558 and sidewalls 1560, 1562, which define the height and width of slot 1556, respectively. Although modular bracket assembly 1500 is depicted with four identical slots 1556, slot 1556 design and quantity may be adjusted without departing from the spirit/scope of the disclosure. For instance, second bracket 1550 may include four variously-sized slots 1556. Second bracket 1550 further includes feature 1566 with surface 1568 for interaction with first bracket 1502, as discussed below.

First bracket 1502 may further include a raised feature (not shown) that is in direct or indirect contact with second bracket 1550. Such feature (not shown) may enable rotation of second bracket 1550 in relation to first bracket 1502. The disclosed feature (not shown) may be a fastener (e.g., screw, pin, etc.) and/or may be a feature fabricated within first bracket 1502 and/or second bracket 1550. Further, although first bracket 1502 and second bracket 1550 are depicted as identically-sized brackets, alternatively-sized brackets may be used.

Sidewalls 1512, 1514, 1560, 1562 are substantially perpendicular to base 1510, 1558. Such orientation provides firm boundaries for constraint of surgical reusable medical devices and/or bracketry. However, sidewalls 1512, 1514, 1560, 1562 may be angled such that the width of base 1510, 1558 is smaller than the opening of slot 1508, 1556, which is located on top surface 1504, 1552. By angling sidewalls 1512, 1514, 1560, 1562, larger-sized reusable medical devices and/or bracketry may be incorporated without altering the perimeter dimensions of bracket 1502, 1550. The width of base 1510, 1558 and the opening of slot 1508, 1556 may be altered to satisfy the intended purpose of modular bracket assembly 1500. Slot 1508, 1556 may further include features (not shown) to assist in inserting reusable medical devices and/or bracketry therein. The design of such features (not shown) may include chamfered edges, radiused edges, as well as other geometries.

As depicted in FIG. 30A, swivel bracket assembly 1500 is depicted in a closed position. The disclosed closed position may include when first bracket 1502 and/or second bracket 1550 is unable to rotate or when reusable medical devices and/or bracketry are in direct or indirect contact with swivel bracket assembly 1500. In an exemplary embodiment, rotation may be restricted by a feature in relation to one or both brackets 1502, 1550. For example, with further reference to FIG. 30B, surface 1520 of feature 1518 may interface with surface 1568 of feature 1566. For illustrative purposes only, if the closed position is considered 0 degrees, second bracket 1550 is unable to rotate clockwise past 0 degrees once surface 1520 makes contact with surface 1568. Additionally, first bracket 1502 may be constrained from rotation as a result of direct or indirect contact with tray 12; however, second bracket 1550 may rotate to allow access to slot 1508. Although feature 1518 is depicted such that rotation to allow access to slot 1508 is in a counterclockwise motion, feature 1518 may be located elsewhere to enable clockwise rotation to access slot 1508.

Further, distance between slot 1508 is generally sized large enough such that when in the open position, second bracket 1550 does not obstruct access to slot 1508. With reference to FIG. 30C, second bracket 1550 may be removed from first bracket 1502 when second bracket 1550 is at an angular orientation less than −360 degrees. In an exemplary embodiment, second bracket 1550 may be separated from first bracket 1502 when surface 1564 of second bracket 1550 is in close proximity to corner 1522 of feature 1518. Removal may also occur by lifting second bracket 1550 vertically away from surface 1504 of first bracket 1502.

Although the present disclosure has been described with reference to exemplary implementations, the present disclosure is not limited by or to such exemplary implementations. Rather, various modifications, refinements and/or alternative implementations may be adopted without departing from the spirit or scope of the present disclosure.

The invention claimed is:

1. A clip, comprising:
   two opposed arms, each of the two opposed arms defining an elongated axis and a mounting structure at an exposed end thereof;
   a bridge connecting the two opposed arms at a location spaced from the mounting structures, the bridge defining an axis that is perpendicular to the elongated axes defined by the two opposed arms; and
   at least one channel defined between the two opposed arms;
   wherein the mounting structure associated with the first of the two opposed arms comprises a first upper extension and a first lower extension,
   wherein the mounting structure associated with the second of the two opposed arms comprises a second upper extension and a second lower extension,
   wherein the first upper extension and the second upper extension (i) extend in a plane that is perpendicular to the elongated axes defined by the two opposed arms, (ii) extend in a plane that is aligned with the axis defined by the bridge, and (iii) extend away from each other;
   wherein the first lower extension and the second lower extension (i) extend in a plane that is perpendicular to the elongated axes defined by the two opposed arms, (ii) extend in a plane that is aligned with the axis defined by the bridge, and (iii) extend away from each other; and
   wherein a first cavity is defined between the first lower extension and the first upper extension, and a second cavity is defined between the second lower extension and the second upper extension.

2. The clip of claim 1, wherein the two opposed arms are at least partially deflectable.

3. The clip of claim 1, wherein the bridge is at least partially deflectable.

4. The clip of claim 1, wherein the two opposed arms and the bridge are fabricated from a material consisting of plastic, silicone, metal and any combination thereof.

5. The clip of claim 4, wherein the two opposed arms and the bridge are fabricated from a thermoplastic.

6. The clip of claim 1, wherein the upper extension is longer than the lower extension.

7. The clip of claim 1, wherein the upper extension and the lower extension are parallel to each other.

8. The clip of claim 1, wherein the mounting structures are configured and dimensioned to engage with an edge of a tray perforation.

9. The clip of claim 8, wherein the cavity of each of the mounting structures is configured and dimensioned to receive an edge of a tray perforation such that the upper extension at least partially engages an upper face of the tray edge and the lower extension at least partially engages a lower face of the tray edge.

10. The clip of claim 8, wherein the mounting structure is configured and dimensioned to supply a spring load to the tray edge.

11. The clip of claim 1, wherein compression of the opposed arms toward each other reduces the size of the at least one channel and causes the distance between the mounting structures to be reduced.

12. The clip of claim 1, wherein the opposed arms extend substantially perpendicularly relative to the bridge.

13. The clip of claim 1, further comprising a bracket associated at least in part with the bridge.

14. A clip, comprising:
   a bridge element defining an axis;
   a first arm and a second arm extending from the bridge element to define a substantially U-shaped structure; and
   a body downwardly extending from the bridge element between the first and second arms, thereby defining (i) a first channel between the first arm and the body, and (ii) a second channel between the second arm and the body;

wherein each of the first and second arms defines an elongated axis and a mounting structure at an exposed end thereof; and wherein each of the first and second arms defines an elongated axis perpendicular to the axis of the bridge and a mounting structure at an exposed end thereof;

wherein the mounting structure associated with the first arm comprises a first upper extension and a first lower extension, wherein the mounting structure associated with the second arm comprises a second upper extension and a second lower extension, wherein the first upper extension and the second upper extension (i) extend in a plane that is perpendicular to the elongated axes defined by the first and second arms, and (ii) extend away from each other;

wherein the first lower extension and the second lower extension (i) extend in a plane that is perpendicular to the elongated axes defined by the first and second arms, and (ii) extend away from each other; and wherein a first cavity is defined between the first lower extension and the first upper extension, and a second cavity is defined between the second lower extension and the second upper extension.

15. The clip of claim 14, wherein the first and second arms are at least partially deflectable.

16. The clip of claim 14, wherein the bridge element is at least partially deflectable.

17. The clip of claim 14, wherein the upper extension is longer than the lower extension.

18. The clip of claim 14, wherein the upper extension and the lower extension are parallel to each other.

19. The clip of claim 14, wherein the body is mounted with respect to a bracket.

20. The clip of claim 14, wherein the mounting structures are configured and dimensioned to engage with an edge of a tray perforation.

21. The clip of claim 20, wherein the cavity of each of the mounting structures is configured and dimensioned to receive an edge of a tray perforation such that the upper extension at least partially engages an upper face of the tray edge and the lower extension at least partially engages a lower face of the tray edge.

22. The clip of claim 20, wherein the mounting structure is configured and dimensioned to supply a spring load to the tray edge.

23. The clip of claim 1, wherein the first and second arms extend substantially perpendicularly relative to the bridge element.

24. A clip, comprising:

two opposed arms, each of the two opposed arms defining an elongated axis and a mounting structure at an exposed end thereof;

a bridge connecting the two opposed arms at a location spaced from the mounting structures, the bridge defining an axis that is perpendicular to the elongated axes defined by the two opposed arms; and at least one channel defined between the two opposed arms;

wherein the mounting structure associated with the first of the two opposed arms comprises a first upper extension and a first lower extension, wherein the mounting structure associated with the second of the two opposed arms comprises a second upper extension and a second lower extension, wherein the first upper extension and the second upper extension (i) extend in a plane that is perpendicular to the elongated axes defined by the two opposed arms, and (ii) extend away from each other;

wherein the first lower extension and the second lower extension (i) extend in a plane that is perpendicular to the elongated axes defined by the two opposed arms, and (ii) extend away from each other;

wherein a first cavity is defined between the first lower extension and the first upper extension, and a second cavity is defined between the second lower extension and the second upper extension;

wherein the first upper extension and the first lower extension are of different lengths; and wherein the second upper extension and the second lower extension are of different lengths.

25. The clip of claim 24, wherein the two opposed arms are at least partially deflectable.

26. The clip of claim 24, wherein the bridge is at least partially deflectable.

27. The clip of claim 24, wherein the upper extension is longer than the lower extension.

28. The clip of claim 24, wherein the upper extension and the lower extension are parallel to each other.

29. The clip of claim 24, wherein the mounting structures are configured and dimensioned to engage with an edge of a tray perforation.

30. The clip of claim 24, further comprising a bracket associated at least in part with the bridge.

* * * * *